(12) United States Patent
Scheib et al.

(10) Patent No.: US 10,258,337 B2
(45) Date of Patent: Apr. 16, 2019

(54) SURGICAL STAPLE CARTRIDGE WITH SEVERED TISSUE EDGE ADJUNCT

(71) Applicant: Ethicon Endo-Surgery, LLC, Guaynabo, PR (US)

(72) Inventors: Charles J. Scheib, Loveland, OH (US); Mark S. Zeiner, Mason, OH (US); Nir I. Nativ, West Orange, NJ (US); Sridevi Dhanaraj, Raritan, NJ (US)

(73) Assignee: Ethicon LLC, Guaynabo, PR (US)

( * ) Notice: Subject to any disclaimer, the term of this patent is extended or adjusted under 35 U.S.C. 154(b) by 275 days.

(21) Appl. No.: 15/133,407

(22) Filed: Apr. 20, 2016

(65) Prior Publication Data

US 2017/0303926 A1    Oct. 26, 2017

(51) Int. Cl.
| | | |
|---|---|---|
| *A61B 17/10* | (2006.01) | |
| *A61B 17/068* | (2006.01) | |
| *A61B 17/32* | (2006.01) | |
| *A61B 17/072* | (2006.01) | |
| *A61B 17/00* | (2006.01) | |

(52) U.S. Cl.
CPC .......... *A61B 17/105* (2013.01); *A61B 17/068* (2013.01); *A61B 17/07207* (2013.01); *A61B 17/07292* (2013.01); *A61B 17/32* (2013.01); *A61B 2017/00477* (2013.01); *A61B 2017/07271* (2013.01); *A61B 2017/07278* (2013.01); *A61B 2017/07285* (2013.01)

(58) Field of Classification Search
CPC ................ A61B 17/105; A61B 17/068; A61B 17/07207; A61B 17/07292; A61B 17/32
USPC ........................................... 227/175.1–180.1
See application file for complete search history.

(56) References Cited

U.S. PATENT DOCUMENTS

| | | | |
|---|---|---|---|
| 4,805,823 | A | 2/1989 | Rothfuss |
| 5,275,323 | A | 1/1994 | Schulze et al. |
| 5,415,334 | A | 5/1995 | Williamson et al. |
| 5,465,895 | A | 11/1995 | Knodel et al. |
| 5,597,107 | A | 1/1997 | Knodel et al. |
| 5,632,432 | A | 5/1997 | Schulze et al. |

(Continued)

FOREIGN PATENT DOCUMENTS

| | | |
|---|---|---|
| EP | 1 064 883 A1 | 1/2001 |
| EP | 1 795 213 A2 | 6/2007 |

(Continued)

OTHER PUBLICATIONS

U.S. Appl. No. 15/147,942, filed May 6, 2016.

(Continued)

*Primary Examiner* — Nathaniel Chukwurah
(74) *Attorney, Agent, or Firm* — Frost Brown Todd LLC

(57) ABSTRACT

An apparatus includes a body assembly, a shaft, an end effector, and a cartridge. The end effector includes a jaw, a pivotable anvil, and a knife member. The cartridge includes a deck, a buttress assembly, and a folding sled. A first portion of the buttress assembly is positioned on top of the deck. A second portion of the buttress assembly is positioned within the longitudinal channel. The folding sled is configured to translate within the longitudinal channel to move the second portion of the buttress assembly to a position that is above the deck in response to actuation of the knife member. The second portion of the buttress assembly is thereby secured against edges of tissue severed by the knife member.

20 Claims, 27 Drawing Sheets

(56) References Cited

U.S. PATENT DOCUMENTS

| | | | |
|---|---|---|---|
| 5,673,840 A | 10/1997 | Schulze et al. | |
| 5,704,534 A | 1/1998 | Huitema et al. | |
| 5,769,892 A | 6/1998 | Kingwell | |
| 5,782,396 A * | 7/1998 | Mastri | A61B 17/07207 227/175.3 |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,273,897 B1 | 8/2001 | Dalessandro et al. | |
| 6,325,810 B1 | 12/2001 | Hamilton et al. | |
| 6,364,888 B1 | 4/2002 | Niemeyer et al. | |
| 6,458,147 B1 | 10/2002 | Cruise | |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,524,320 B2 | 4/2009 | Tierney et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,141,762 B2 | 3/2012 | Bedi et al. | |
| 8,210,411 B2 | 7/2012 | Yates et al. | |
| 8,308,042 B2 | 11/2012 | Aranyi et al. | |
| 8,371,491 B2 | 2/2013 | Huitema et al. | |
| 8,408,439 B2 | 4/2013 | Huang et al. | |
| 8,453,914 B2 | 6/2013 | Laurent et al. | |
| 8,479,969 B2 | 7/2013 | Shelton | |
| 8,573,461 B2 | 11/2013 | Shelton et al. | |
| 8,573,465 B2 | 11/2013 | Shelton | |
| 8,602,288 B2 | 12/2013 | Shelton | |
| 8,616,431 B2 | 12/2013 | Timm et al. | |
| 8,657,176 B2 | 2/2014 | Shelton, IV et al. | |
| 8,746,535 B2 | 6/2014 | Shelton, IV et al. | |
| 8,783,541 B2 | 7/2014 | Shelton et al. | |
| 8,800,838 B2 | 8/2014 | Shelton | |
| 8,801,735 B2 | 8/2014 | Shelton et al. | |
| 8,814,025 B2 | 8/2014 | Miller et al. | |
| 8,820,605 B2 | 9/2014 | Shelton | |
| 8,844,789 B2 | 9/2014 | Shelton et al. | |
| 8,864,009 B2 | 10/2014 | Shelton, IV et al. | |
| 8,899,464 B2 | 12/2014 | Hueil et al. | |
| 8,998,060 B2 | 4/2015 | Bruewer et al. | |
| 9,044,227 B2 | 6/2015 | Shelton et al. | |
| 9,101,359 B2 | 8/2015 | Smith et al. | |
| 9,113,865 B2 | 8/2015 | Shelton, IV et al. | |
| 9,113,873 B2 | 8/2015 | Marczyk et al. | |
| 9,168,038 B2 | 10/2015 | Shelton, IV et al. | |
| 9,186,142 B2 | 11/2015 | Fanelli et al. | |
| 9,198,644 B2 | 12/2015 | Balek et al. | |
| 9,198,662 B2 | 12/2015 | Barton et al. | |
| 9,211,120 B2 | 12/2015 | Scheib et al. | |
| 9,220,501 B2 | 12/2015 | Baxter, III et al. | |
| 9,241,714 B2 | 1/2016 | Timm et al. | |
| 9,301,759 B2 | 4/2016 | Spivey et al. | |
| 9,393,018 B2 | 7/2016 | Wang et al. | |
| 9,398,911 B2 | 7/2016 | Auld | |
| 9,402,627 B2 | 8/2016 | Stevenson et al. | |
| 9,717,821 B2 | 8/2017 | Schutte et al. | |
| 2006/0062768 A1 | 3/2006 | Hnojewyj | |
| 2008/0169328 A1 | 7/2008 | Shelton | |
| 2011/0104280 A1 | 5/2011 | Hnojewyj | |
| 2012/0125792 A1 | 5/2012 | Cassivi | |
| 2012/0241493 A1 | 9/2012 | Baxter et al. | |
| 2013/0037596 A1 | 2/2013 | Bear et al. | |
| 2013/0062391 A1 | 3/2013 | Boudreaux et al. | |
| 2013/0068816 A1 | 3/2013 | Vasudevan et al. | |
| 2013/0075447 A1 | 3/2013 | Weisenburgh et al. | |
| 2013/0206813 A1 | 8/2013 | Nalagatla | |
| 2013/0214030 A1 | 8/2013 | Aronhalt et al. | |
| 2013/0221062 A1 * | 8/2013 | Hodgkinson | A61B 17/072 227/176.1 |
| 2014/0001239 A1 * | 1/2014 | Shelton, IV | A61B 17/105 227/176.1 |
| 2014/0110455 A1 * | 4/2014 | Ingmanson | A61B 17/072 227/176.1 |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239042 A1 | 8/2014 | Simms et al. | |
| 2014/0239043 A1 | 8/2014 | Simms et al. | |
| 2014/0239044 A1 | 8/2014 | Hoffman | |
| 2014/0239047 A1 | 8/2014 | Hodgkinson et al. | |
| 2014/0263563 A1 | 9/2014 | Stokes et al. | |
| 2015/0272575 A1 | 10/2015 | Leimbach et al. | |
| 2015/0296297 A1 | 10/2015 | Hua et al. | |
| 2015/0351754 A1 | 12/2015 | Harris et al. | |
| 2015/0351758 A1 | 12/2015 | Shelton et al. | |
| 2015/0351763 A1 | 12/2015 | Shelton et al. | |
| 2015/0374360 A1 | 12/2015 | Scheib et al. | |
| 2015/0374373 A1 | 12/2015 | Rector et al. | |
| 2016/0089146 A1 | 3/2016 | Harris et al. | |
| 2016/0278774 A1 | 9/2016 | Shelton, IV et al. | |

FOREIGN PATENT DOCUMENTS

| | | |
|---|---|---|
| EP | 2 462 880 A2 | 6/2012 |
| EP | 2 586 380 A1 | 5/2013 |
| EP | 2 742 872 A1 | 6/2014 |
| EP | 2 764 827 A2 | 8/2014 |
| WO | WO 2015/146548 A1 | 4/2017 |

OTHER PUBLICATIONS

U.S. Appl. No. 14/827,856, filed Aug. 17, 2015.
U.S. Appl. No. 14/840,613, filed Aug. 31, 2015.
U.S. Appl. No. 14/871,071, filed Sep. 30, 2015.
U.S. Appl. No. 14/871,131, filed Sep. 30, 2015.
European Search Report and Written Opinion dated Jul. 3, 2017 for Application No. EP 17167158.9, 10 pgs.
International Search Report and Written Opinion dated Jun. 30, 2017 for Application No. PCT/US2017/028560, 13 pgs.
International Search Report and Written Opinion dated Jul. 19, 2017 for Application No. PCT/US2017/030383, 16 pgs.

* cited by examiner

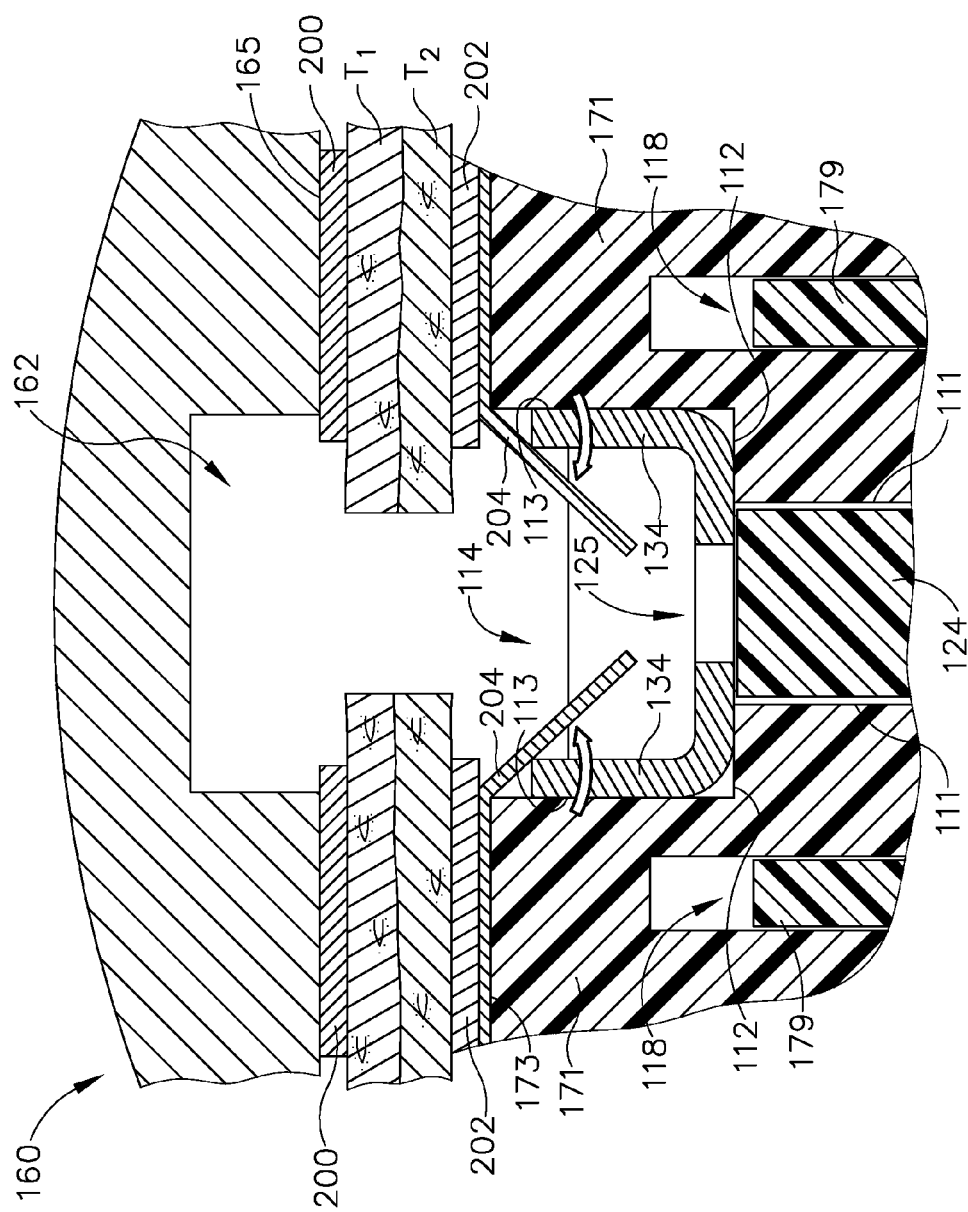

SURGICAL STAPLE CARTRIDGE WITH SEVERED TISSUE EDGE ADJUNCT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014, now U.S. Pat. No. 9,168,142, issued Nov. 17, 2015; U.S. Patent Pub. No. 2014/0239041, entitled "Lockout Feature for Movable Cutting Member of Surgical Instrument," published Aug. 28, 2014, now U.S. Pat. No. 9,717,497, issued Aug. 1, 2017; U.S. Patent Pub. No. 2014/0239042, entitled "Integrated Tissue Positioning and Jaw Alignment Features for Surgical Stapler," published Aug. 28, 2014, now U.S. Pat. No. 9,517,065, issued Dec. 13, 2016; U.S. Patent Pub. No. 2014/0239036, entitled "Jaw Closure Feature for End Effector of Surgical Instrument," published Aug. 28, 2014, now U.S. Pat. No. 9,839,421, issued Dec. 12, 2017; U.S. Patent Pub. No. 2014/0239040, entitled "Surgical Instrument with Articulation Lock having a Detenting Binary Spring," published Aug. 28, 2014, now U.S. Pat. No. 9,867,615, issued Jan. 1, 2018; U.S. Patent Pub. No. 2014/0239043, entitled "Distal Tip Features for End Effector of Surgical Instrument," published Aug. 28, 2014, now U.S. Pat. No. 9,622,746, issued Apr. 18, 2017; U.S. Patent Pub. No. 2014/0239037, entitled "Staple Forming Features for Surgical Stapling Instrument," published Aug. 28, 2014, now U.S. Pat. No. 10,092,292, issued Oct. 9, 2018; U.S. Patent Pub. No. 2014/0239038, entitled "Surgical Instrument with Multi-Diameter Shaft," published Aug. 28, 2014, now U.S. Pat. No. 9,795,379, issued Oct. 24, 2017; and U.S. Patent Pub. No. 2014/0239044, entitled "Installation Features for Surgical Instrument End Effector Cartridge," published Aug. 28, 2014, now U.S. Pat. No. 9,808,248, issued Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014, now U.S. Pat. No. 9,597,082, issued Mar. 21, 2017; U.S. Pub. No.

2014/0246473, entitled "Rotary Powered Surgical Instruments with Multiple Degrees of Freedom," published Sep. 4, 2014, now U.S. Pat. No. 9,398,911, issued Jul. 16, 2016; U.S. Pub. No. 2013/0206813, entitled "Linear Stapler," published Aug. 15, 2013; now abandoned; U.S. Pub. No. 2008/0169328, entitled "Buttress Material for Use with a Surgical Stapler," published Jul. 17, 2008, now abandoned; U.S. Pub. No. 2015/0351754, entitled "Woven and Fibrous Materials for Reinforcing a Staple Line," published Dec. 10, 2015, now U.S. Pat. No. 9,848,871, issued Dec. 26, 2017; U.S. Pub. No. 2015/0351763, entitled "Devices and Methods for Sealing Staples in Tissue," published Dec. 10, 2015, now U.S. Pat. No. 9,936,954, issued Apr. 10, 2018; and U.S. Pub. No. 2016/0089146, entitled "Radically Expandable Staple Line," published Mar. 31, 2016. The disclosure of each of the above-cited U.S. Patents and U.S. Patent Publications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples. In addition or in the alternative, such a buttress may reduce bleeding at the site of the staples and the adjacent cuts in tissue. While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 18C depicts a cross-sectional front view of the end effector of FIG. 5, where the secondary folding sled of FIG. 9 has further folded a portion of the buttress of the end effector, where the knife member has severed tissue.

Figure 1:
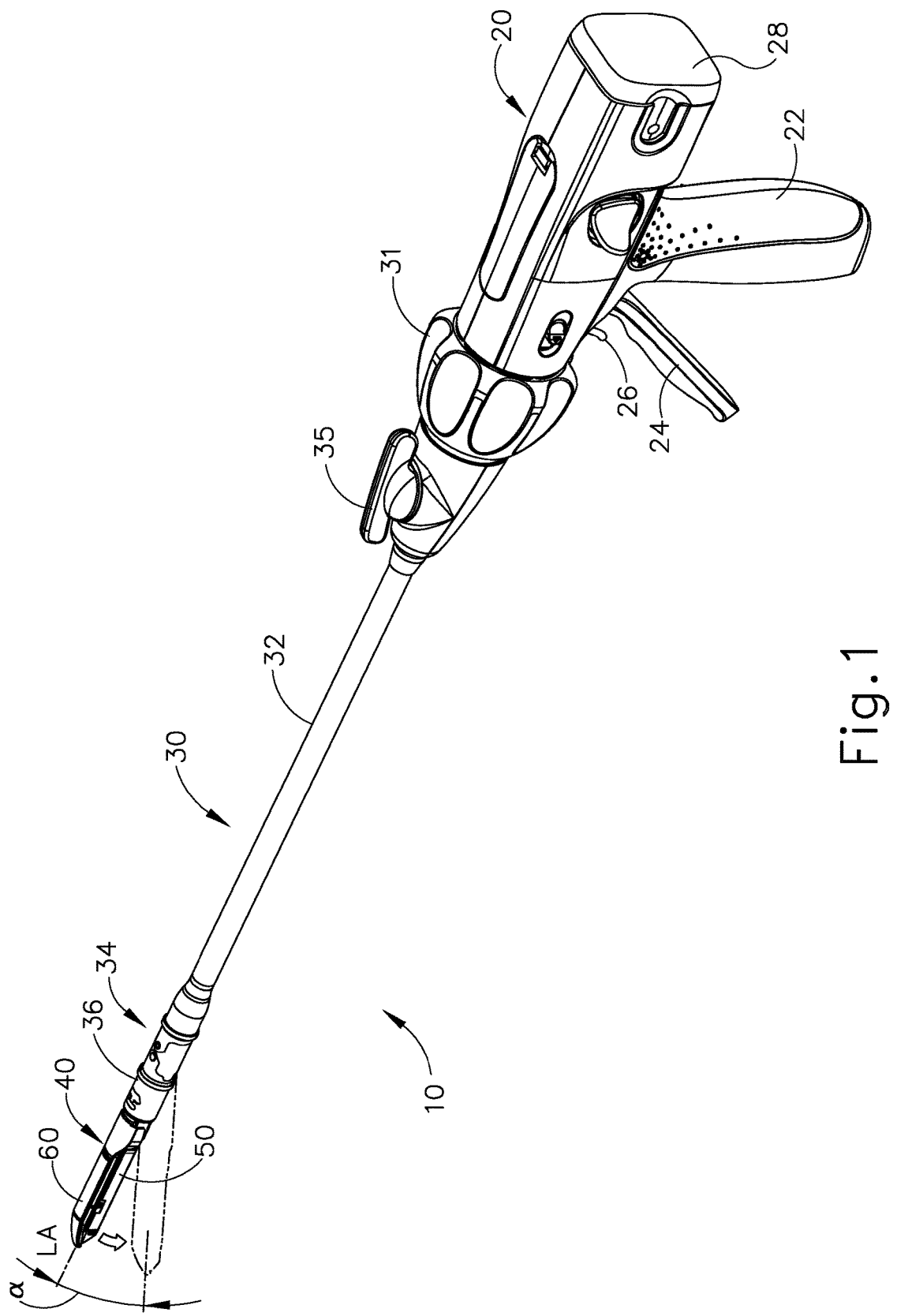
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 2:
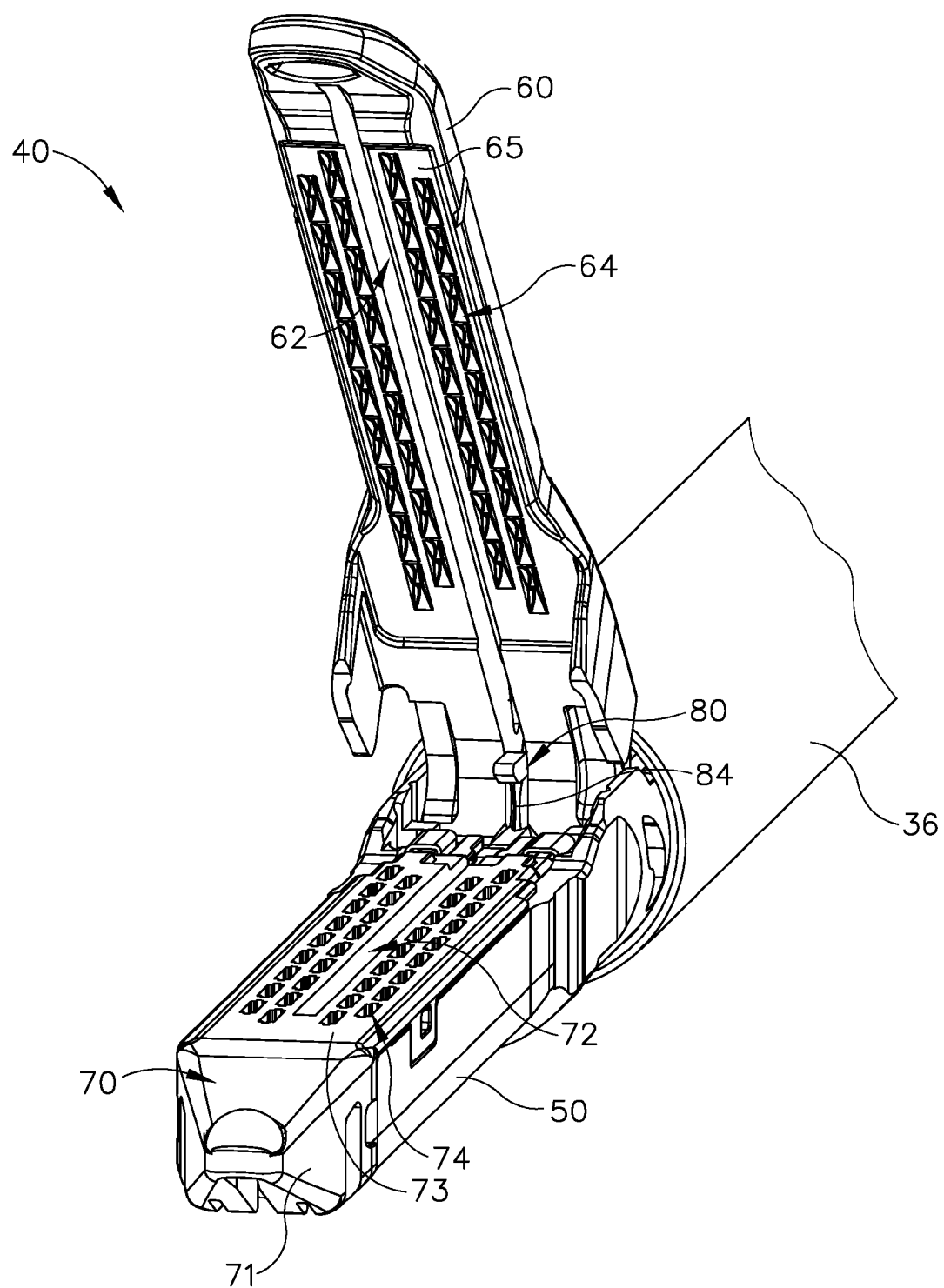
FIG. 2 depicts a perspective view of an end effector of the instrument of FIG. 1, with the end effector in an open configuration.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (α). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, now U.S. Pat. No. 9,186,142, issued Nov. 17, 2015, the disclosure of which is incorporated by reference herein; and/or U.S. Pub. No. 2015/0374360, entitled "Articulation Drive Features for Surgical Stapler," published Dec. 31, 2015, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, now U.S. 9,795,379, issued Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 3:
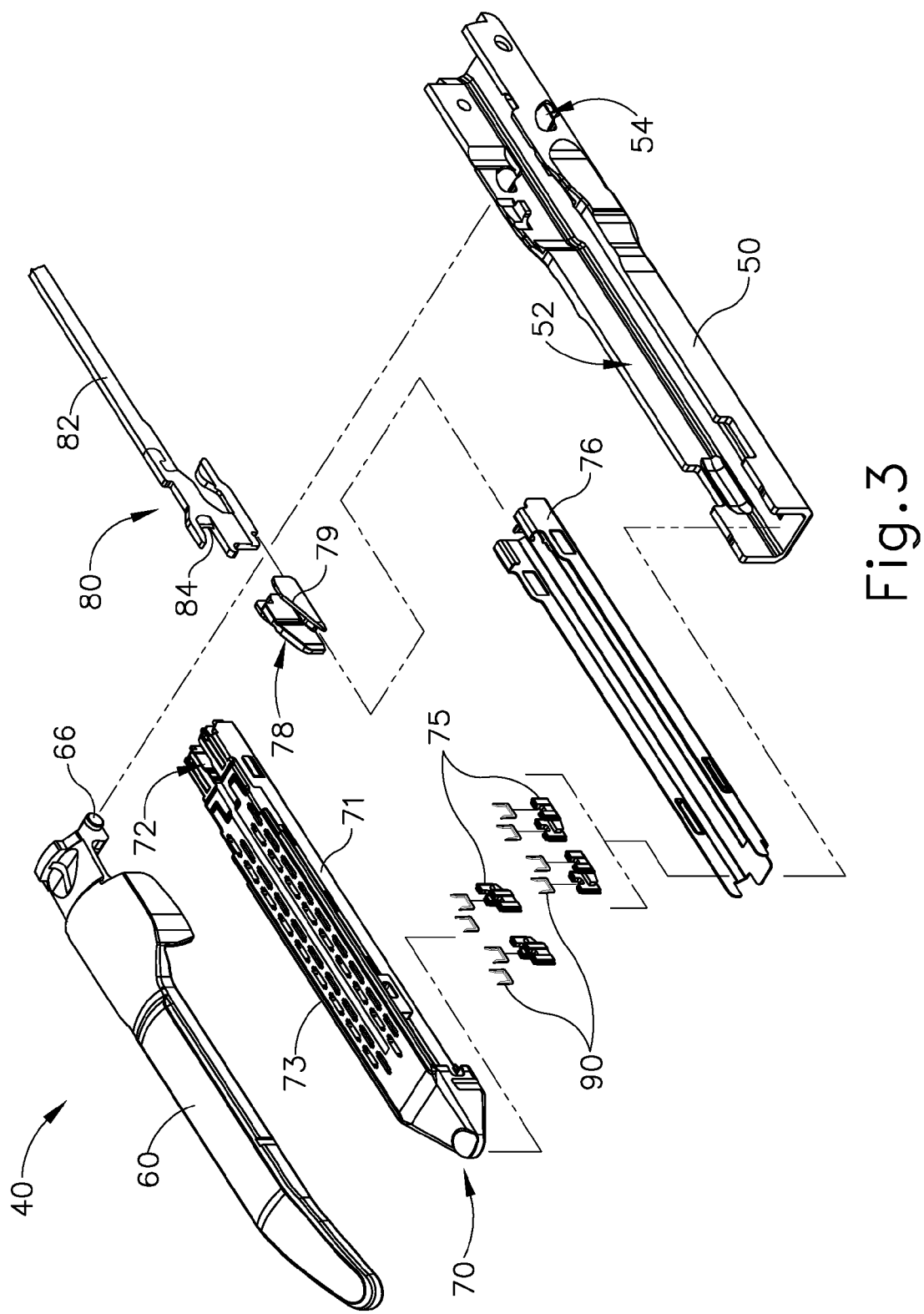
FIG. 3 depicts an exploded perspective view of the end effector of FIG. 2.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, now U.S. Pat. No. 9,808,248, issued Nov. 7, 2017, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position, staple drivers (75) are in downward positions and staples (90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U. U.S. Pub. No. 2014/0239042, entitled "Integrated Tissue Positioning and Jaw Alignment Features for Surgical Stapler," published Aug. 28, 2014, now U.S. Pat. No. 9,517,065, issued Dec, 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, now U.S. Pat. No. 9,808,248, issued Nov. 7, 2017, the disclosure of which is incorporated by reference herein. Other suitable forms that staple cartridge (70) may take will be apparent to those of ordinary skill in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014; now U.S. Pat. No. 9,517,065, issued Dec. 13, 2016; at least some of the teachings of U.S. Pub. No. 2014/0239036, entitled "Jaw Closure Feature for End Effector of Surgical Instrument," published Aug. 28, 2014; now U.S. Pat. No. 9,839,421, issued Dec. 12, 2017; and/or at least some of the teachings of U.S. Pub. No. 2014/0239037, entitled "Staple Forming Features for Surgical Stapling Instrument," published Aug. 28, 2014, now U.S. Pat. No. 10,092,292, issued Oct. 9, 2018, the disclosure of which is incorporated by reference herein. Other suitable forms that anvil (60) may take will be apparent to those of ordinary skill in the art in view of the teachings herein.

In the present example, a knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil

(60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, now U.S. Pat. No. 9,839,421, issued Dec. 12, 2017, the disclosure of which is incorporated by reference herein; and/or in accordance with at least some of the teachings of U.S. Pub. No. 2015/0374373, entitled "Jaw Opening Feature for Surgical Stapler," published Dec. 31, 2015, the disclosure of which is incorporated by reference herein.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also in the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein.; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. Pub. No. 2015/0272575, entitled "Surgical Instrument Comprising a Sensor System," published Oct. 1, 2015, now U.S. Pat. No. 9,913,642, issued Mar. 13, 2018, the disclosure of which is incorporated by reference herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary End Effectors with Buttress for Surgical Stapler

In some instances, it may be desirable to equip end effector (40) with a buttress material and/or other kind of adjunct(s). Such a buttress material and/or other kind of adjunct(s) may serve a variety of purposes, including but not limited to reinforcing the mechanical fastening of tissue provided by staples (90). Such a buttress may prevent the applied staples (90) from pulling through the tissue and may otherwise reduce a risk of tissue tearing at or near the site of applied staples (90). In addition to or as an alternative to providing structural support and integrity to a line of staples (90), a buttress and/or other adjunct(s) may provide various other kinds of effects such as spacing or gap-filling (e.g., taking up gaps otherwise formed by uneven anatomical surfaces, to promote substantially even compression forces across the length and width of end effector (40)), administration of therapeutic agents (e.g., to promote hemostasis in tissue engaged by end effector (40)), and/or other effects. While the term "buttress" will be used throughout the following discussion, it should be understood that the use of the term "buttress" is not intended to place any limitation on the functionality of the buttress. The term "buttress" should therefore be read as applying to any structure that provides an adjunct to end effector (40), serving any suitable functional purpose with respect to the tissue engaged by end effector (40).

In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various ways in which a buttress may be secured to a staple cartridge (70) or an anvil (60) will also be described in greater detail below.

It should be understood that the buttresses described below may be constructed and operable in accordance with at least some of the teachings of U.S. Pat. No. 9,044,227, entitled "Collapsible Fastener Cartridge," issued Jun. 2, 2015, the disclosure of which is incorporated by reference herein; U.S. Patent Pub. No. 2012/0241493, entitled "Tissue Thickness Compensator Comprising Controlled Release and Expansion," published Sep. 27, 2012, now U.S. Pat. No. 10,123,798, issued Nov. 13, 2018, the disclosure of which is incorporated by reference herein; U.S. Patent Pub. No. 2013/0068816, entitled "Surgical Instrument and Buttress Material," published Mar. 21, 2013, now abandoned, the disclosure of which is incorporated by reference herein; U.S. Patent Pub. No. 2013/0062391, entitled "Surgical Instrument with Fluid Fillable Buttress," published Mar. 14, 2013, now U.S. Pat. No. 9,999,408, issued Jun. 19, 2018, the disclosure of which is incorporated by reference herein; U.S. Patent Pub. No. 2013/0068820, entitled "Fibrin Pad Matrix with Suspended Heat Activated Beads of Adhesive," published Mar. 21, 2013, now U.S. Pat. No. 8,814,025, issued Aug. 26, 2014, the disclosure of which is incorporated by reference herein; U.S. Patent Pub. No. 2013/0082086, entitled "Attachment of Surgical Staple Buttress to Cartridge," published Apr. 4, 2013, now U.S. Pat. No. 8,899, 464, issued Dec. 2, 2014, the disclosure of which is incorporated by reference herein; U.S. Patent Pub. No. 2013/0037596, entitled "Device for Applying Adjunct in Endoscopic Procedure," published Feb. 14, 2013, now U.S. Pat. No. 9,492,170, issued Nov. 15, 2016, the disclosure of which is incorporated by reference herein; U.S. Patent Pub. No. 2013/0062393, entitled "Resistive Heated Surgical Staple Cartridge with Phase Change Sealant," published Mar. 14, 2013, now U.S. Pat. No. 8,998,060, issued Apr. 7, 2015, the disclosure of which is incorporated by reference herein; U.S. Patent Pub. No. 2013/0075446, entitled "Surgical Staple Assembly with Hemostatic Feature," published Mar. 28, 2013, now U.S. Pat. No. 9,393,018, issued Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, now U.S. Pat. No. 9,101,359, issued Aug. 11, 2015, the disclosure of which is incorporated by reference herein; U.S. Patent Pub. No. 2013/0075445, entitled "Anvil Cartridge for Surgical Fastening Device," published Mar. 28, 2013, now U.S. Pat. No. 9,198,644, issued Dec. 1, 2015, the disclosure of which is incorporated by reference herein; U.S. Patent Pub. No. 2013/0075447, entitled "Adjunct Therapy for Applying Hemostatic Agent," published Mar. 28, 2013, now abandoned, the disclosure of which is incorporated by reference herein; U.S. Patent Pub. No. 2013/0256367, entitled "Tissue Thickness Compensator Comprising a Plurality of Medicaments," published Oct. 3, 2013, now U.S. Pat. No. 9,211,120, issued Dec. 15, 2015, the disclosure of which is incorporated by reference herein; U.S. patent application Ser. No. 14/300,954, entitled "Adjunct Materials and Methods of Using Same in Surgical Methods for Tissue Sealing," filed Jun. 10, 2014, now U.S. Pat. No. 10,172,611, issued Jan. 8, 2019, the disclosure of which is incorporated by reference herein; U.S. patent application Ser. No. 14/667,842, entitled "Method of Applying a Buttress to a Surgical Stapler," filed Mar. 25, 2015, published as U.S. Patent Pub. No. 2016/0278774, on Sep. 29, 2016, the disclosure of which is incorporated by reference herein; U.S. patent application Ser. No. 14/827,856, entitled "Implantable Layers for a Surgical Instrument," filed Aug. 17, 2015, published as U.S. Patent Pub. No. 2017/0049444, on Feb. 23, 2017, the disclosure of which is incorporated by reference herein; U.S. patent application Ser. No. 14/840,613, entitled "Drug Eluting Adjuncts and Methods of Using Drug Eluting Adjuncts," filed Aug. 31, 2015, published as U.S. Patent Pub. No. 2017/0055986, on Mar. 2, 2017, the disclosure of which is incorporated by reference herein; U.S. patent application Ser. No. 14/871,071, entitled "Compressible Adjunct with Crossing Spacer Fibers," filed Sep. 30, 2015, published as U.S. Patent Pub. No. 2017/0086837, Mar. 30, 2017, the disclosure of which is incorporated by reference herein; and/or U.S. patent application Ser. No. 14/871,131, entitled "Method for Applying an Implantable Layer to a Fastener Cartridge," filed Sep. 30, 2015, published as U.S. Patent Pub. No. 2017/0086842, on Mar. 30, 2017, the disclosure of which is incorporated by reference herein. Alternatively, the buttresses described below may be constructed and operable in any other suitable fashion.

A. Exemplary Buttress

Figure 4:
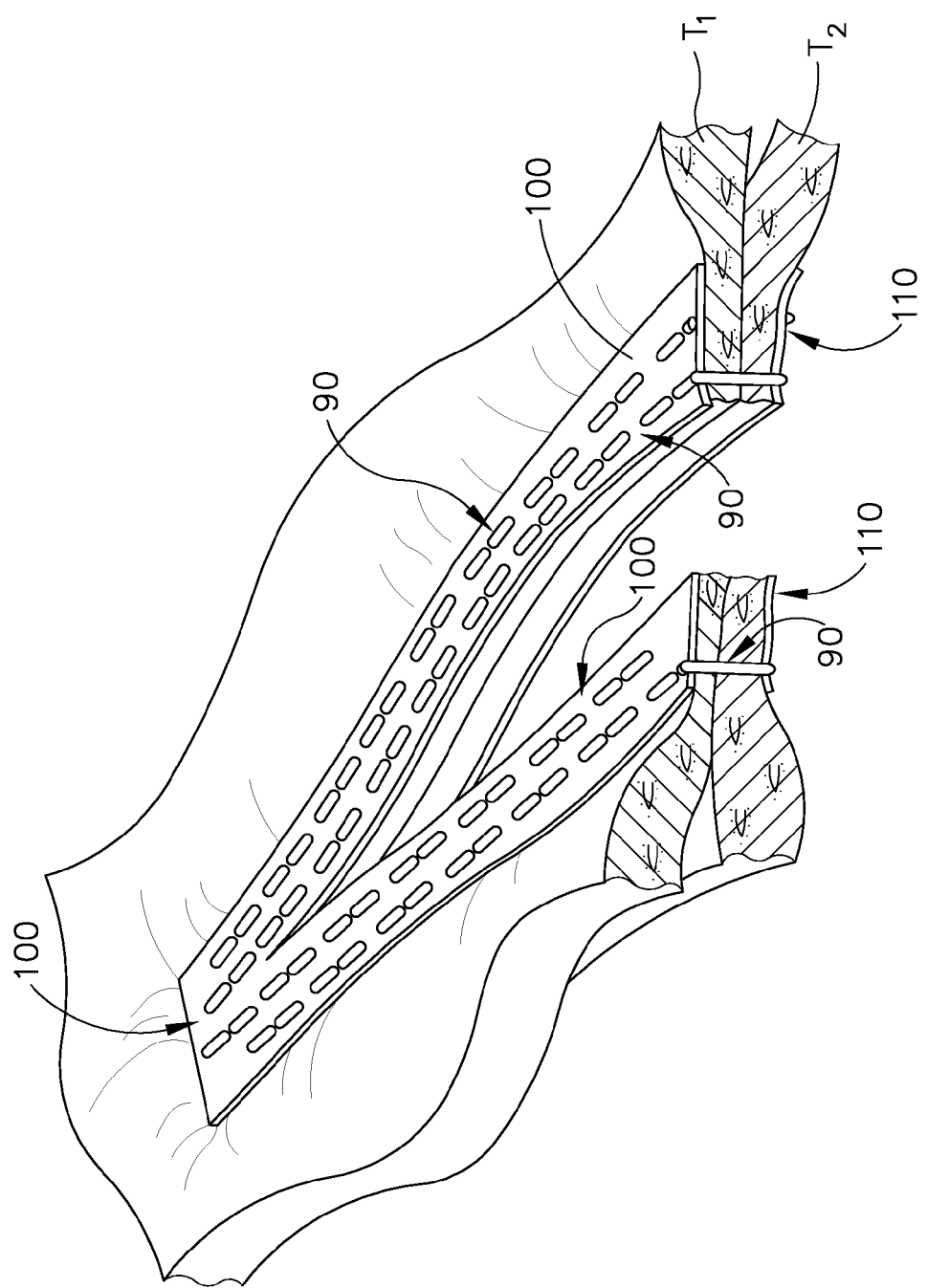
FIG. 4 depicts a perspective view of staples and an exemplary buttress assembly that may be installed on the end effector of FIG. 2, with the staples and buttress assembly having been secured to tissue by the end effector of FIG. 2.

FIG. 4 shows the end result of where end effector (40) has been loaded with a first buttress (100) on deck (73) of cartridge (70) and a second buttress (110) on underside (65) of anvil (60), and where end effector (40) has been actuated to drive staples through apposed layers of tissue ($T_1$, $T_2$) while also severing apposed layers of tissue ($T_1$, $T_2$). First buttress (100) and second buttress (110) may be attached to deck (73) and underside (65) of anvil (60) with adhesives or using any other suitable method known to one having ordinary skill in the art in view of the teachings herein. Several of the above-cited references teach various suitable ways in which buttresses (100, 110) may be attached to deck (73) and underside (65) of anvil (60).

It should be understood that a series of staples (90) will similarly capture and retain buttresses (100, 110) against layers of tissue ($T_1$, $T_2$), thereby securing buttresses (100, 110) to tissue ($T_1$, $T_2$) as shown in FIG. 4. As end effector (40) is pulled away from tissue (90) after deploying staples (90) and buttresses (100, 110), buttresses (100, 110) disengage end effector, such that buttresses (100, 110) remain secured to tissue ($T_1$, $T_2$) with staples (90). Buttresses (100, 110) thus provides structural reinforcement to the lines of staples (90). As can also be seen in FIG. 4, knife member (80) also cuts through a centerline of buttresses (100, 110), separating each buttress (100, 110) into a corresponding pair of sections, such that each section remains secured to a respective severed region of tissue ($T_1$, $T_2$). It should be understood that the severed edges of apposed layers of tissue ($T_1$, $T_2$) are not in contact with buttresses (100, 110).

In the foregoing example, buttress assembly (100) is sized to span across the full width of underside (65), such that buttress assembly (100) spans across channel (62). Thus, knife member (80) cuts through buttress assembly (100) during actuation of end effector (40) as described above. In some other examples, such as those described below, buttress assembly (100) is provided in two separate, laterally spaced apart portions, with one buttress portion being disposed on underside (65) on one side of channel (62) and another buttress portion being disposed on underside (65) on the other side of channel (62). In such versions, buttress assembly (100) does not span across channel (62), such that knife member (80) does not cut through buttress assembly (100) during actuation of end effector (40).

Likewise, buttress assembly (110) may be sized to span across the full width of deck (73), such that buttress assembly (110) spans across channel (72), and such that knife member (80) cuts through buttress assembly (110) during actuation of end effector (40) as described above. Alternatively in some other examples, such as those described below, buttress assembly (110) may be provided in two separate, laterally spaced apart portions, with one buttress portion being disposed on deck (73) on one side of channel (72) and another buttress portion being disposed on deck (73) on the other side of channel (72), such that buttress assembly (110) does not span across channel (72), and such that knife member (80) does not cut through buttress assembly (110) during actuation of end effector (40).

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, published as U.S. Patent Pub. No. 2016/0278774, on Sep. 29, 2016, the disclosure of which is incorporated by reference herein; and/or in accordance with the teachings of any other references cited herein.

B. Alternative End Effector for Applying Buttress to Severed Tissue Edge

In some instances it may be desirable to apply a buttress material to the severed edges of tissue ($T_1$, $T_2$) created by actuation of knife member (80). In such cases, it may also be desirable to include haemostatic agents or other adjuncts to the buttress material to further treat the newly severed edges of tissue ($T_1$, $T_2$). Additionally, it may also be desirable to include adhesives to the buttress material to ensure that the buttress material remains in contact with severed edges of tissue ($T_1$, $T_2$) after the buttress material is applied. Applying the buttress material directly to severed edges of tissue ($T_1$, $T_2$) may lead to a reduced amount of bleeding, faster healing of severed edges of tissue ($T_1$, $T_2$), and/or other results.

Figure 5:
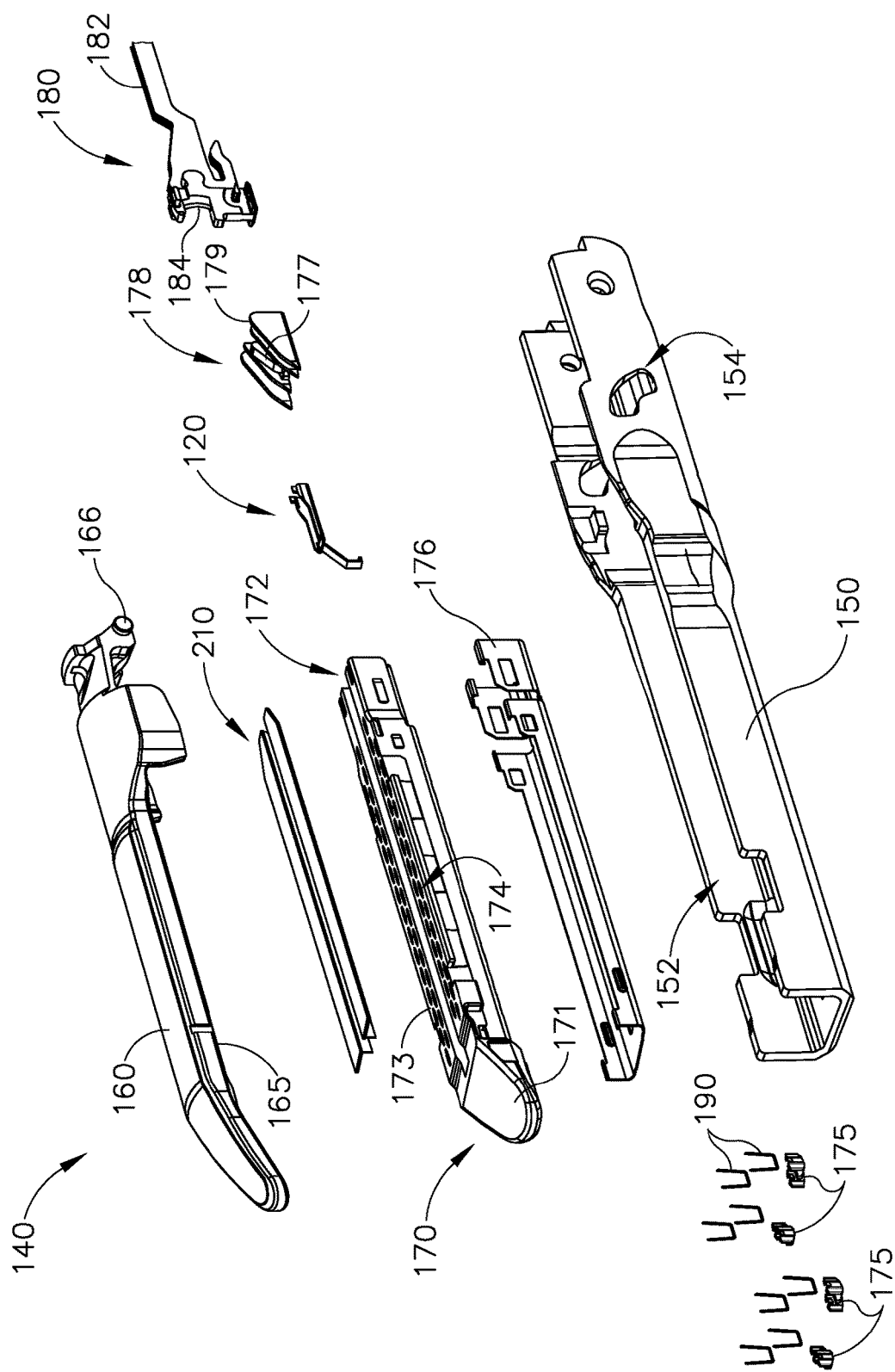
FIG. 5 depicts an exploded view of an alternative end effector that may be incorporated into the instrument of FIG. 1.
Figure 6:
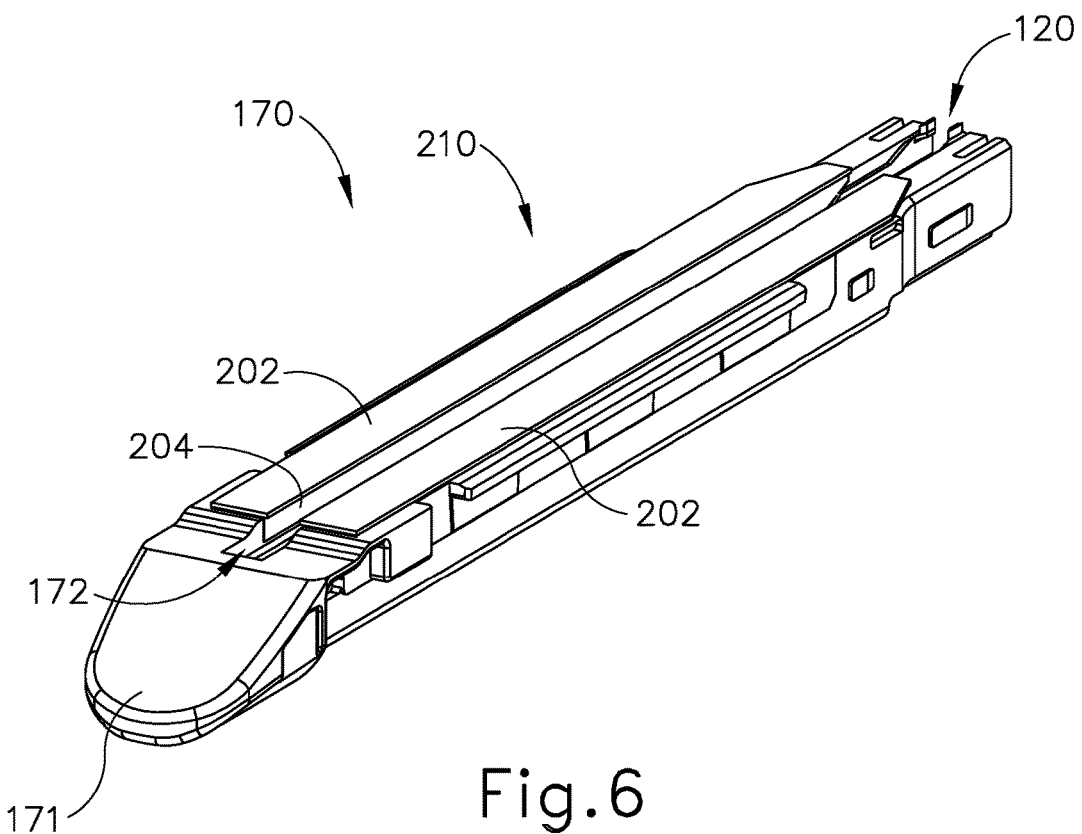
FIG. 6 depicts a perspective view of the end effector of FIG. 5.
Figure 7:
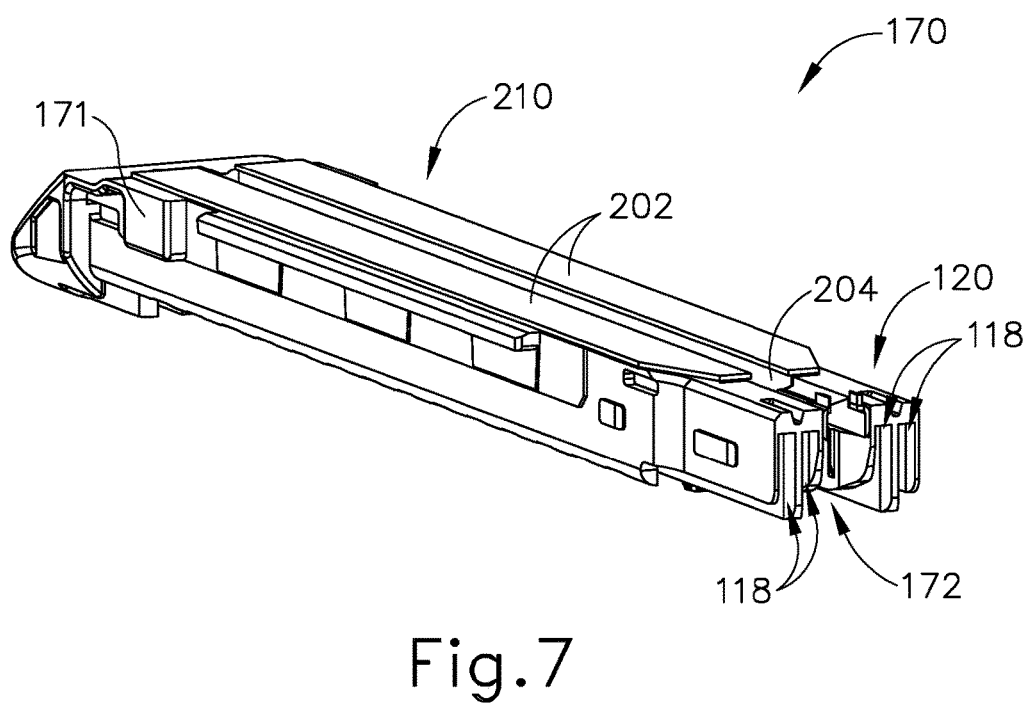
FIG. 7 depicts another perspective view of the end effector of FIG. 5.

FIG. 5 shows an alternative end effector (140) that may be readily incorporated into instrument (10) described above. End effector (140) of this example includes a lower jaw (150) and a pivotable anvil (160), which are substantially similar to lower jaw (50) and pivotable anvil (60) described above, respectively. Therefore, anvil (160) is pivotable toward and away lower jaw (150) via a pair of integral, outwardly extending pins (166) that are disposed in corresponding curved slots (154) of lower jaw (150).

Lower jaw (150) defines a channel (152) that is configured to receive a staple cartridge (170). Staple cartridge (170) is substantially similar to staple cartridge (70) mentioned above, with differences described in further detail below. Therefore, staple cartridge (170) may be inserted into channel (152), end effector (140) may be actuated, and then staple cartridge (170) may be removed and replaced with another staple cartridge (170). Lower jaw (150) thus releasably retains staple cartridge (170) in alignment with anvil (160) for actuation of end effector (40). Other suitable forms that lower jaw (150) may take will be apparent to those of ordinary skill in the art in view of the teachings herein.

Staple cartridge (170) of the present example includes a cartridge body (171) and a tray (176) secured to the underside of cartridge body (171). The upper side of cartridge body (171) presents a deck (173), against which a portion of a buttress assembly (210) may be placed on top of as will be described in greater detail below. Cartridge body (171) further defines a longitudinally extending channel (172) and a plurality of staple pockets (174). A staple (190) is positioned in each staple pocket (174). A staple driver (175) is also positioned in each staple pocket (174), underneath a corresponding staple (190), and above tray (176). As will be described in greater detail below, staple drivers (175) are operable to translate upwardly in staple pockets (174) to thereby drive staples (190) upwardly through staple pockets (174) and buttress assembly (210) and into engagement with anvil (160). Staple drivers (175) are driven upwardly by a wedge sled (178), which is captured between cartridge body (171) and tray (176), and which translates longitudinally through cartridge body (171).

Wedge sled (178) includes a plurality of obliquely angled cam surfaces (179) and a secondary sled driver (177). As will be described in greater detail below, secondary sled driver (177) is configured to actuate against and drive a folding sled (120), which in turn folds a portion of buttress assembly (210) against newly severed edges of tissue ($T_1$, $T_2$).

Obliquely angled cam surfaces (179) are dimensioned to translate within longitudinal cam channels (118) defined by cartridge (171). It should be understood that longitudinal cam channels (118) are in communication with staple pockets (174). Therefore, obliquely angled cam surfaces (179) are configured to engage staple drivers (175) and thereby drive staple drivers (175) upwardly as wedge sled (178) translates longitudinally distally through cartridge (170). For instance, when wedge sled (178) is in a proximal position, staple drivers (175) are in downward positions and staples (190) are located in staple pockets (174). As wedge sled (178) is driven to the distal position by a translating knife member (180), wedge sled (178) drives staple drivers (175) upwardly, thereby driving staples (190) out of staple pockets (174) and into staple forming pockets (164) that are formed in the underside (165) of anvil (160). Thus, staple drivers (175) translate along a vertical dimension as wedge sled (178) translates along a horizontal dimension.

Anvil (160) of the present example includes a longitudinally extending channel (162) and a plurality of staple forming pockets (not shown), which are substantially similar to longitudinally extending channel (62) and plurality of staple forming pockets (64) described above, respectively. Therefore, channel (162) is configured to align with channel (172) of staple cartridge (170) when anvil (160) is in a closed position in such a way as to deform legs of staples (190) when staples (190) are driven through tissue and into anvil (160). In particular, staple forming pockets (not shown) are configured to bend legs of staples (190) to secure the formed stapled (190) into the tissue.

In the present example, a knife member (180) is configured to translate longitudinally through end effector (140). Knife member (180) is substantially similar to knife member (80) mentioned above with differenced described below. As best seen in FIG. 5, knife member (180) is secured to the distal end of a firing beam (182), which extends through a portion of shaft assembly (30). Knife member (180) is positioned in channels (162, 172) of anvil (160) and staple cartridge (170). Knife member (180) includes a distally presented cutting edge (184) that is configured to sever tissue compressed between anvil (160) and deck (173) of staple cartridge (170) as knife member (180) translates distally through end effector (140). As noted above, knife member (180) also drives wedge sled (178) distally as knife member (180) translates distally through end effector (140), thereby driving staples (190) through tissue and against anvil (160).

Figure 8:
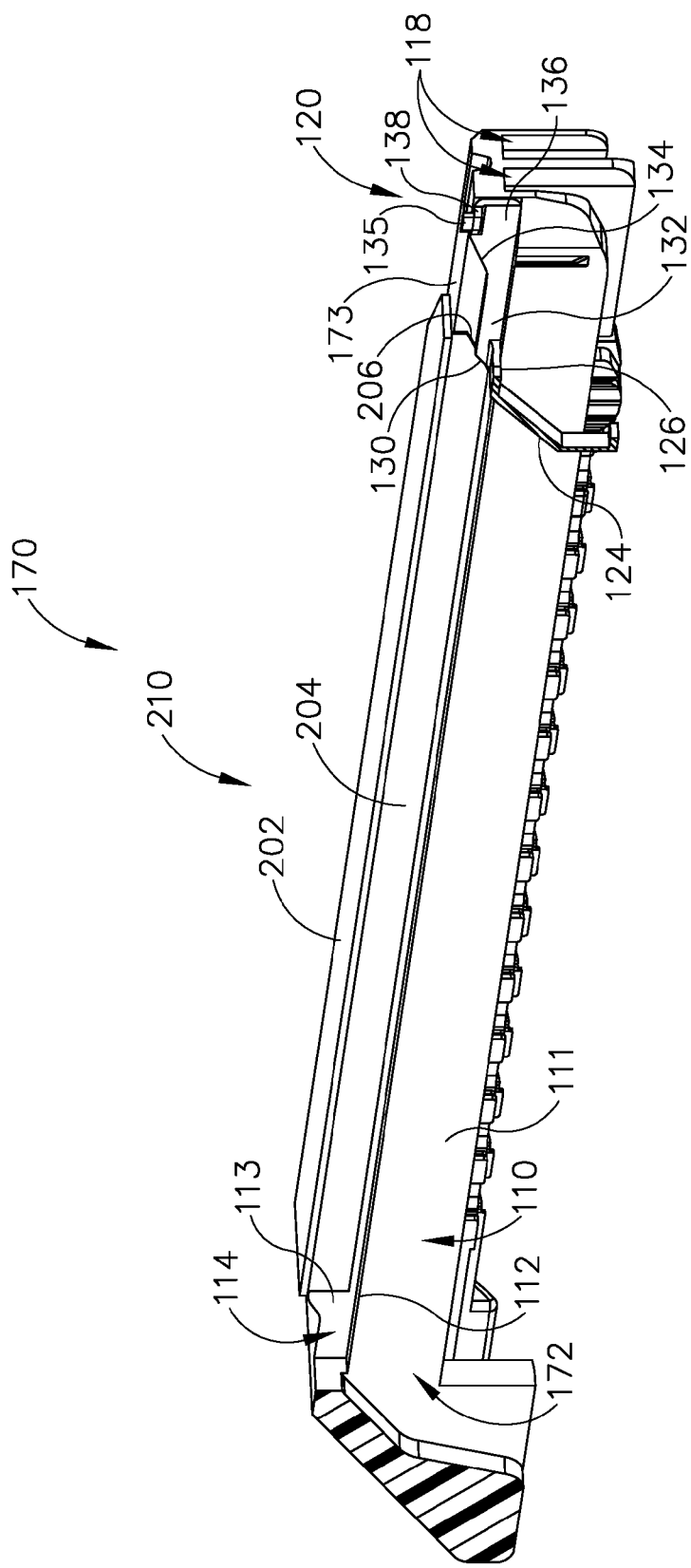
FIG. 8 depicts a cross-sectional perspective view of the end effector of FIG. 5.
Figure 9:
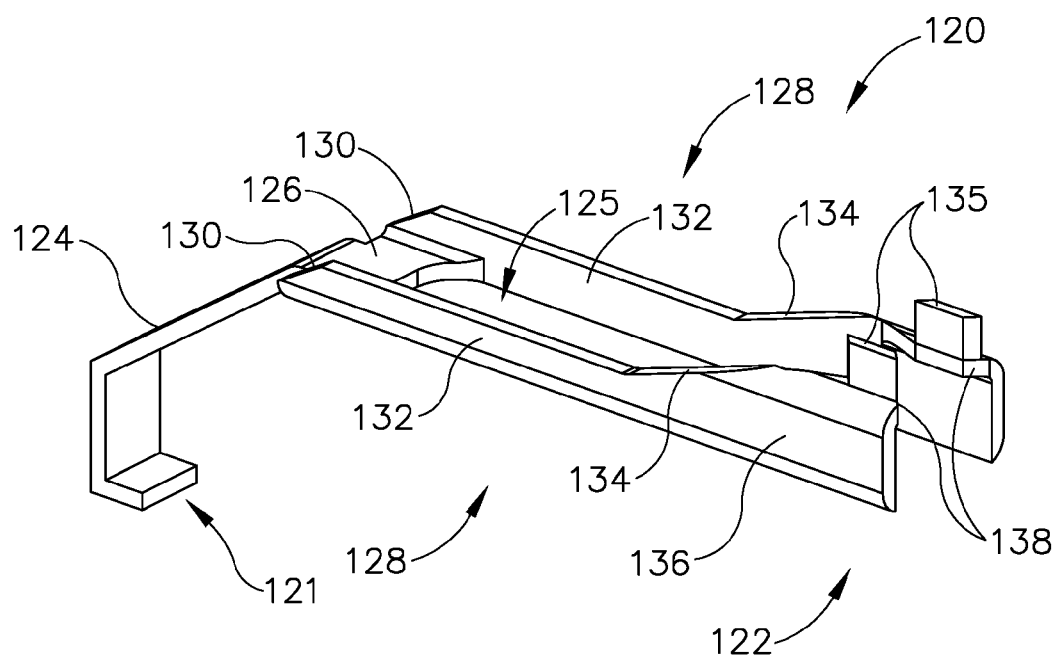
FIG. 9 depicts a perspective view of the secondary folding sled of the end effector of FIG. 5.
Figure 10:
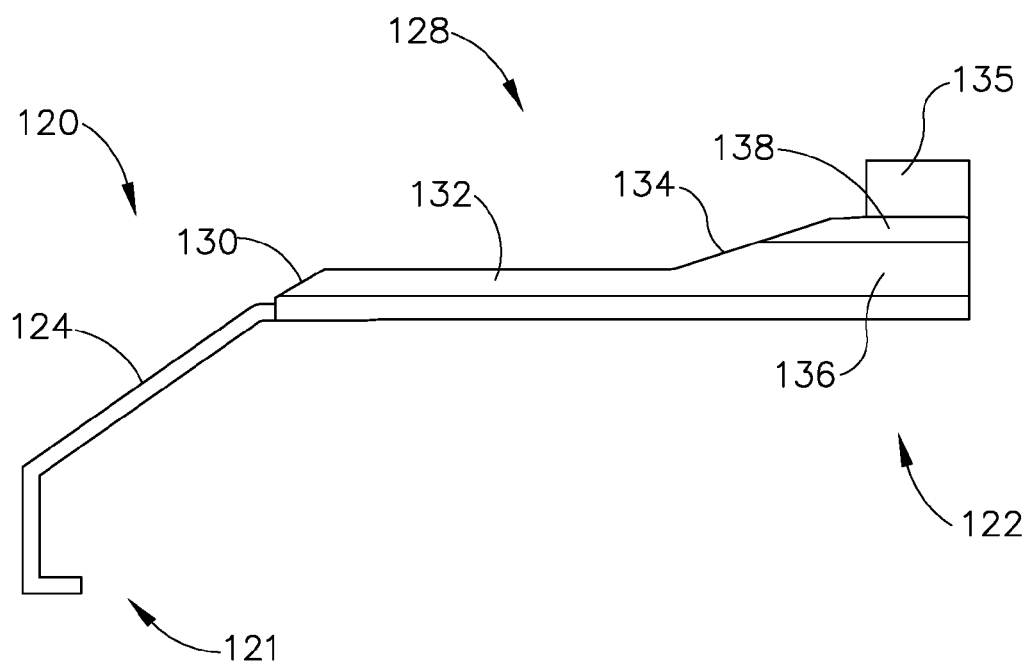
FIG. 10 depicts a side elevational view of the secondary folding sled of FIG. 9.
Figure 11:
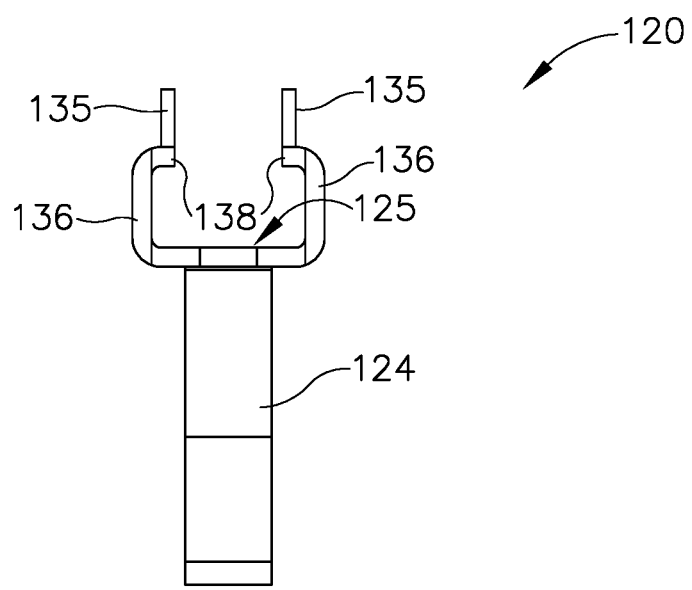
FIG. 11 depicts a front elevational view of the secondary folding sled of FIG. 9.
Figure 12:
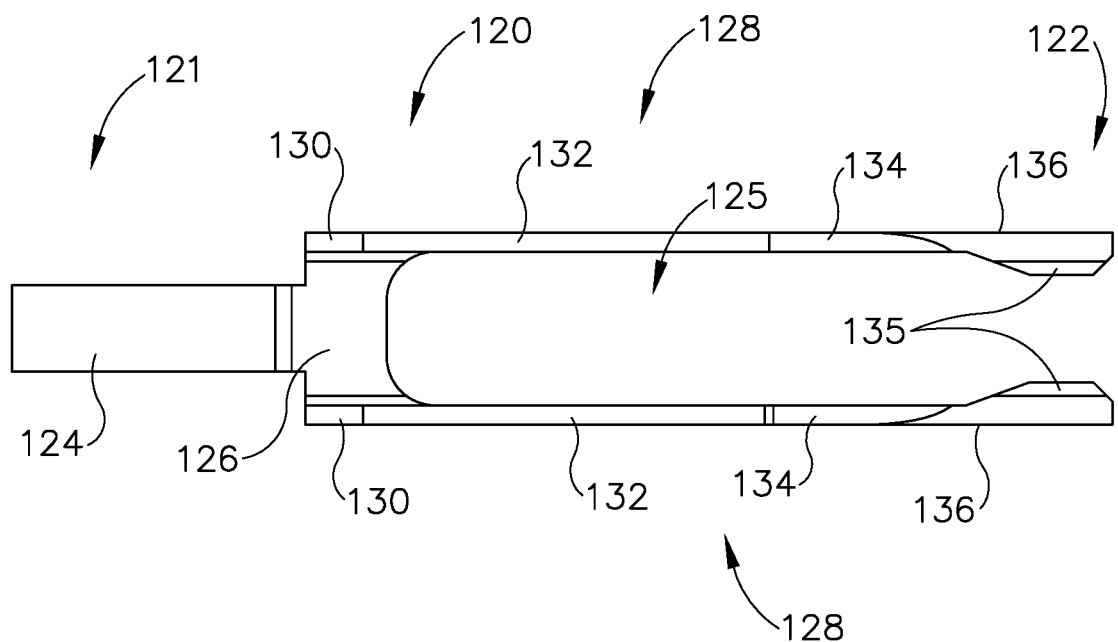
FIG. 12 depicts a top plan view of the secondary folding sled of FIG. 9.
Figure 13:
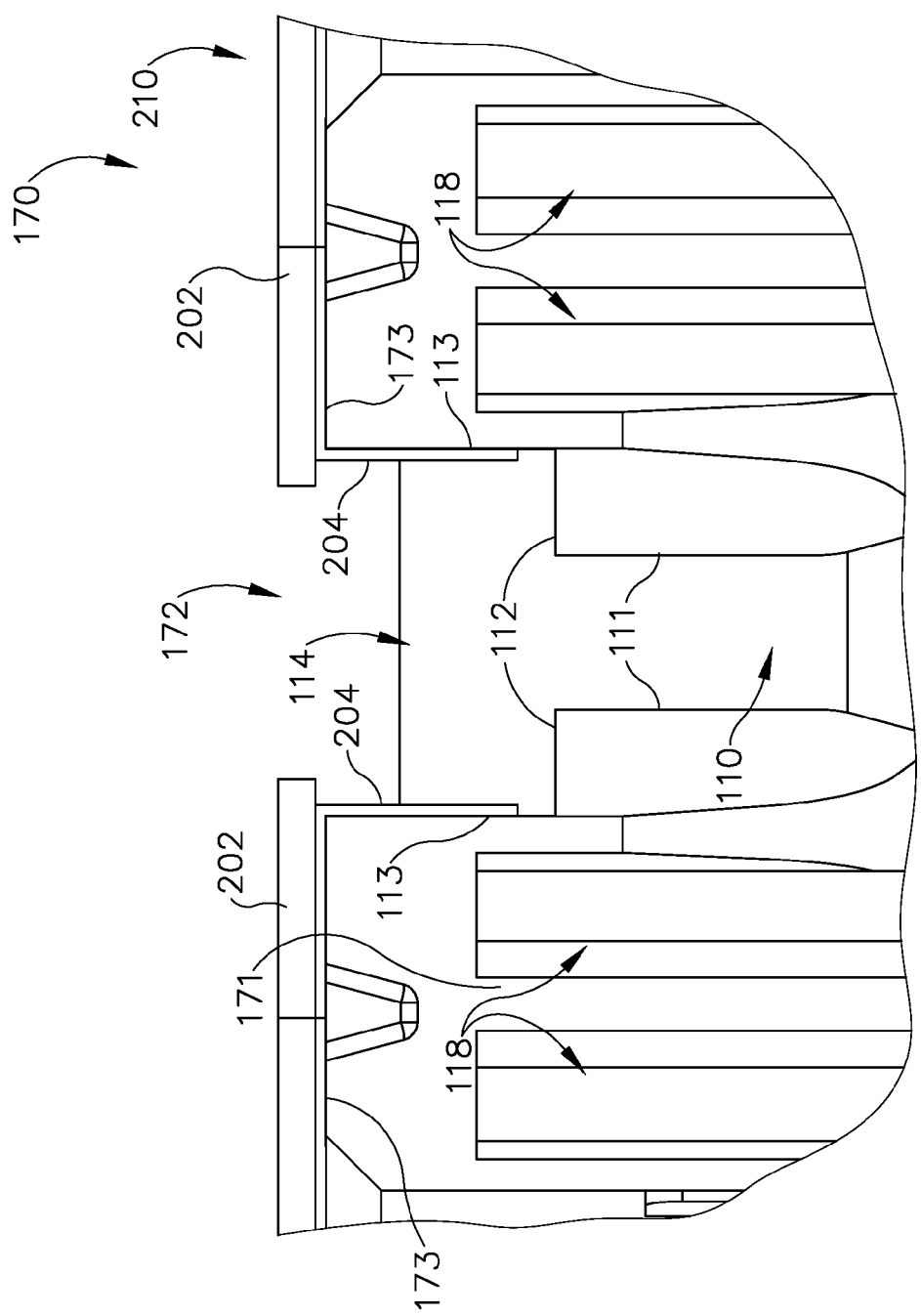
FIG. 13 depicts a cross-sectional front view of the staple cartridge of the end effector of FIG. 5.
Figure 14:
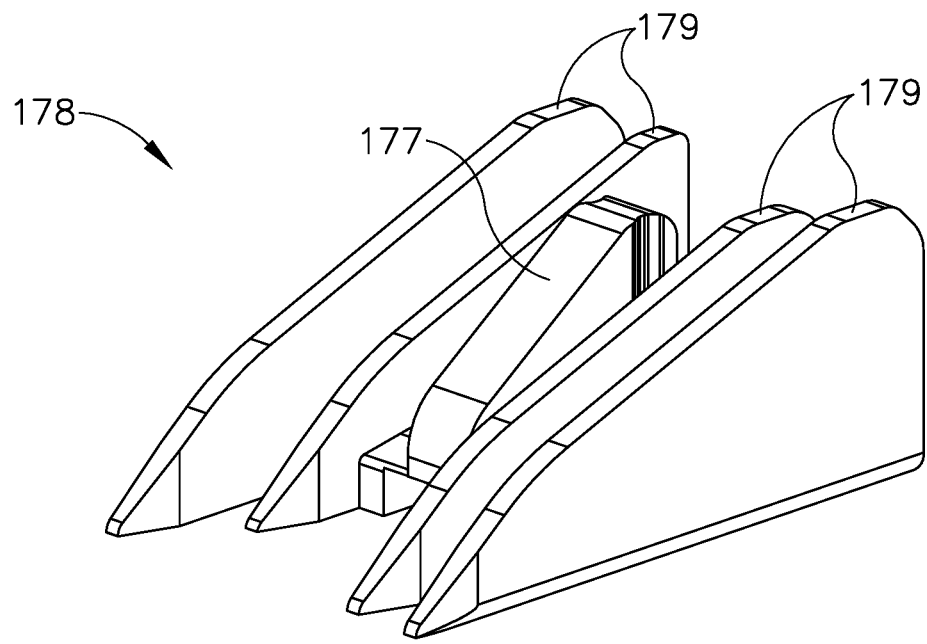
FIG. 14 depicts a perspective view of the wedge sled of the end effector of FIG. 5.
Figure 15:
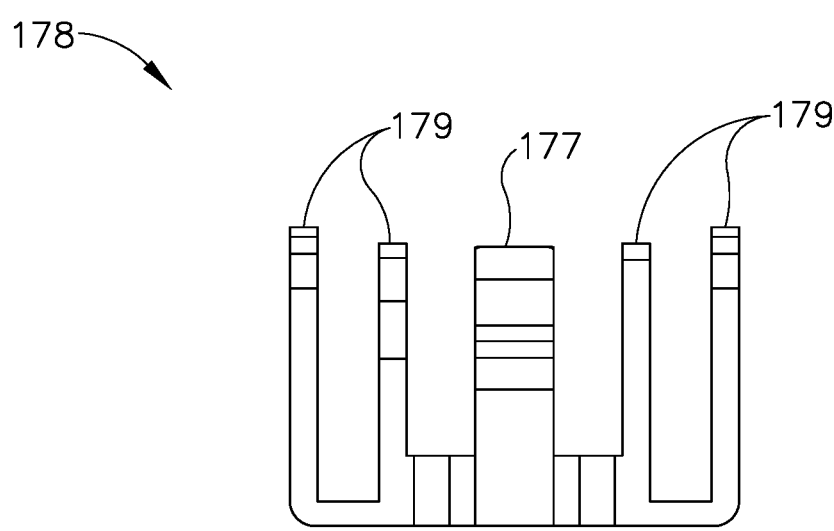
FIG. 15 depicts a rear elevational view of the wedge sled of FIG. 14.

As mentioned above, cartridge body (171) defines a longitudinal channel (172). As best seen in FIGS. 8 and 13, longitudinal channel (172) includes a narrow portion (110) and a wide portion (114). Narrow portion (110) is defined by narrow vertical walls (111) that extend from the underside of cartridge body (171) to a pair of steps (112). Wide portion (114) is defined by wide vertical walls (112) that extend from steps (112) to deck (173). In other words, steps (112) help define a transition between narrow portion (110) and wide portion (114).

As mentioned above, a portion of buttress assembly (210) is placed on top of deck (173). As best seen in FIGS. 6-8 and 13, buttress assembly (210) includes a pair of top buttresses (202) and a pair of bottom folding buttresses (204). Each underside of top buttress (202) is connected to a corresponding bottom folding buttress (204). Bottom folding buttress (204) may be secured to the underside of top buttress (202) through use of adhesives or any other suitable connection as would be apparent by one having ordinary skill in the art in view of the teachings herein. In some alternative versions, buttresses (202, 204) are formed together unitarily, such that the body of folding buttress (204) is simply a downwardly extending portion of the body of top buttress (202).

Each bottom folding buttress (204) is also secured to both deck (173) and a corresponding wide vertical wall (113) defining wide portion (114) of longitudinal channel (172). Each bottom folding buttress (204) may be removably secured to deck (173) and wide vertical wall (113) through adhesives or any other suitable means known to one in the art in view of the teachings herein. By way of example only each bottom folding buttress (204) may be removably secured to deck (173) and wide vertical wall (113) in accordance with the teachings of any of the various references cited herein that relate to buttresses. It should be understood that the portion of bottom folding buttress (204) connected to deck (173) may be secured by different means as compared to the portion of folding buttress (204) connected to wide vertical walls (113). In the current example, a portion of bottom folding buttress (204) is connected to both top buttress (202) and deck (173), however this is merely optional. For example, bottom folding buttress (204) may be connected to a portion of top buttress (202) directly adjacent to longitudinal channel (172). In such an example, top buttress (202) may be directly connected to deck (173) while bottom folding buttress (202) extends from the edge of top buttress (202) toward wide vertical wall (113). Alternatively, top buttress (202) may be omitted entirely.

In some instances, the portion of bottom folding buttress (204) connected to wide vertical wall (113) may not be secured to wide vertical wall (113), but merely extend along wide portion (114) of longitudinal channel (172). For example, the portion of bottom folding buttress (204) associated with wide vertical wall (113) may be folded relative to deck (173) toward wide vertical wall (113). Additionally, the portion of bottom folding buttress (204) associated with wide vertical wall (113) may be sturdy enough to maintain its folded position within wide portion (114) of longitudinal channel (172), but pliable enough to fold in response to an external force.

As mentioned above, cartridge (170) also includes folding sled (120). Folding sled (120) is slidably disposed within longitudinal channel (172) of cartridge (170). As will be described in greater detail below, folding sled (120) is configured to fold the portion of bottom folding buttress (204) associated with wide vertical wall (113) above deck (173) such that bottom folding buttress (204) contacts severed edges of tissue ($T_1$, $T_2$).

Folding sled (120) includes a hooked projection (124) connected to a pair of elongated arms (128) via a coupling member (126). Hooked projection (124) is located at a distal portion (121) of folding sled (120), while elongated arms (128) extend from coupling member (126) to a proximal portion (122) of folding sled (120). Coupling member (126) and elongated arms (128) define a slot (125) for knife member (180) to travel through, as will be described in greater detail below.

Hooked projection (124) is narrower than the gap between elongated arms (128). Hooked projection (124) is dimensioned to be slidably received within narrow portion (110) of longitudinal channel (172). As will be described in greater detail below, hooked projection (124) is dimensioned to receive secondary sled driver (177) of wedge sled (178) such that longitudinal translation of wedge sled (178) also translates folding sled (120) along longitudinal channel (172).

As mentioned above, coupling member (126) connects hooked projection (124) with elongated arms (128). Coupling member (126) is dimensioned such that elongated arms (128) rest on corresponding steps (112) of longitudinal channel (172). Therefore, elongated arms (128) may slide on top of steps (112) of longitudinal channel (172). Elongated arms (128) each include a rail (132) and a folding portion (136). Rail (132) extends from coupling member (126), at a distal end; and toward folding portion (136), at a proximal end. The distal end of rail (132) terminates into a distal sloped surface (130).

Folding portion (136) includes a sloped surface (134), an inward projection (138), and a fin (135). Sloped surface (134) extends from the proximal end of rail (132) toward inward projection (138); while inward projection (138) is connected to fins (135), which extend above inward projection (138). Inward projections (138) face toward each other and longitudinal channel (172). As will be described in greater detail below, fins (135) and inward projections (138) are dimensioned to ensure that portions of bottom folding buttress (204) associated with wide vertical walls (113) are rotated relative to wide vertical walls (113) such that bottom folding buttresses (204) ultimately extend above deck (173) and generally perpendicularly relative to deck (173).

In the current example, fins (135) are generally planar and rectangular. However any other suitable geometric shape may be utilized as would be apparent to one having ordinary skill in the art in view of the teachings herein. For example, fins (135) may be generally triangular or rhomboidal. It should also be understood that folding portion (136) may have a variety of tapered edges in order to promote rotating of buttress assembly (210) relative to wide vertical walls (113), as will be described in greater detail below. Any suitable combination and/or geometry of tapered edges may be utilized as would be apparent to one having ordinary skill in the art in view of the teachings herein.

FIGS. 16A-16E show a sequence of knife member (180), secondary sled driver (177) of wedge sled (178), and folding sled (20) actuating from a proximal position to a distal position within longitudinal channel (172) of cartridge body (171); while FIGS. 17A-17E show the same sequence without knife member (180) for purposes of clarity. It should be understood that FIGS. 16A-17E do not show anvil (160) for purposes of clarity, although in exemplary use, anvil (160) would be in a closed position relative to cartridge (170). Additionally, it should be understood that FIGS. 16A-17E purposefully omit the firing of staples (190) as described above for purposes of clarity. However, it should be understood that staples (190) would be fired above deck (173) and through top buttress (202) in response to longitudinal translation of obliquely angled cam surfaces (179) underneath corresponding staple pockets (174).

Figure 16A:
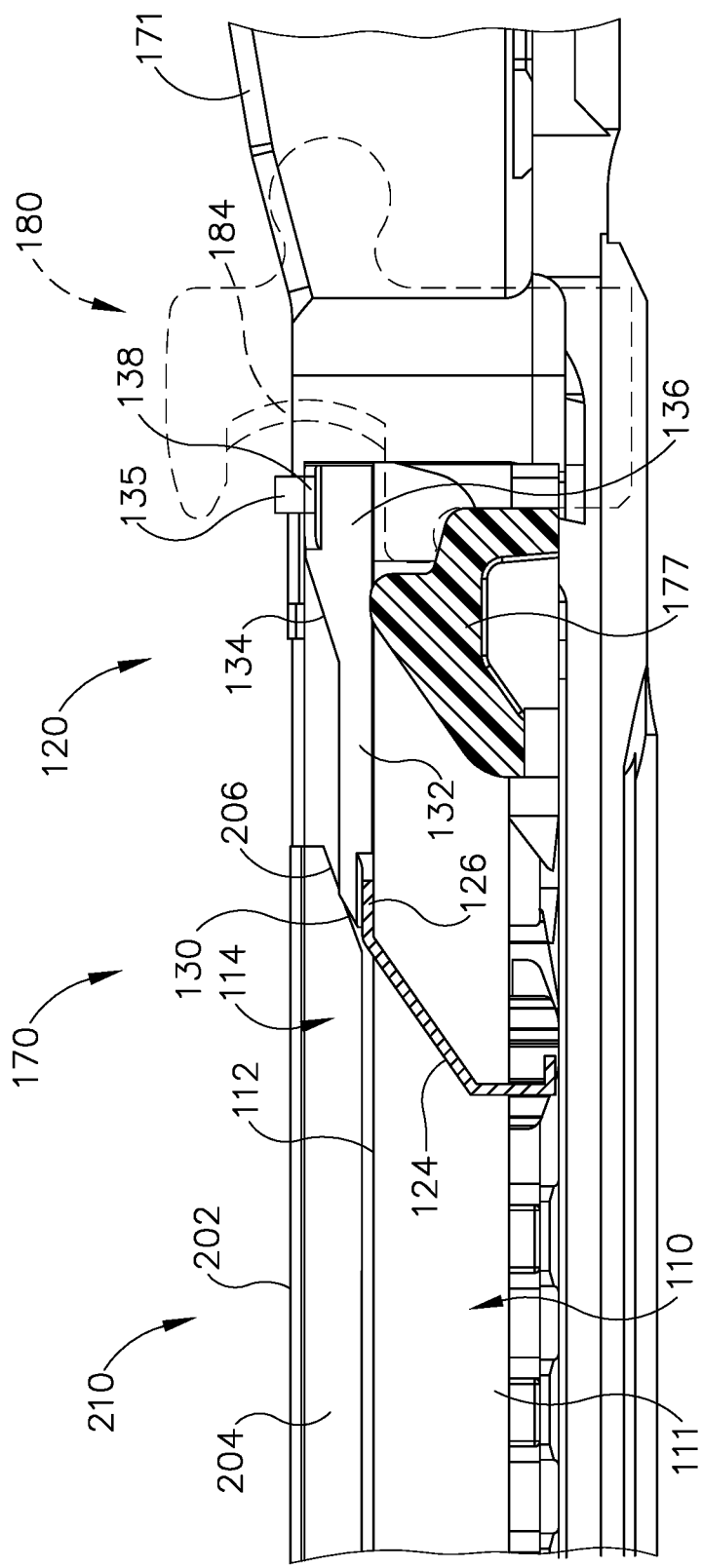
FIG. 16A depicts a cross-sectional side view of the end effector of FIG. 5, where the secondary folding sled of FIG. 9 and the wedge sled of FIG. 14 are each in an unactuated, proximal position.
Figure 16B:
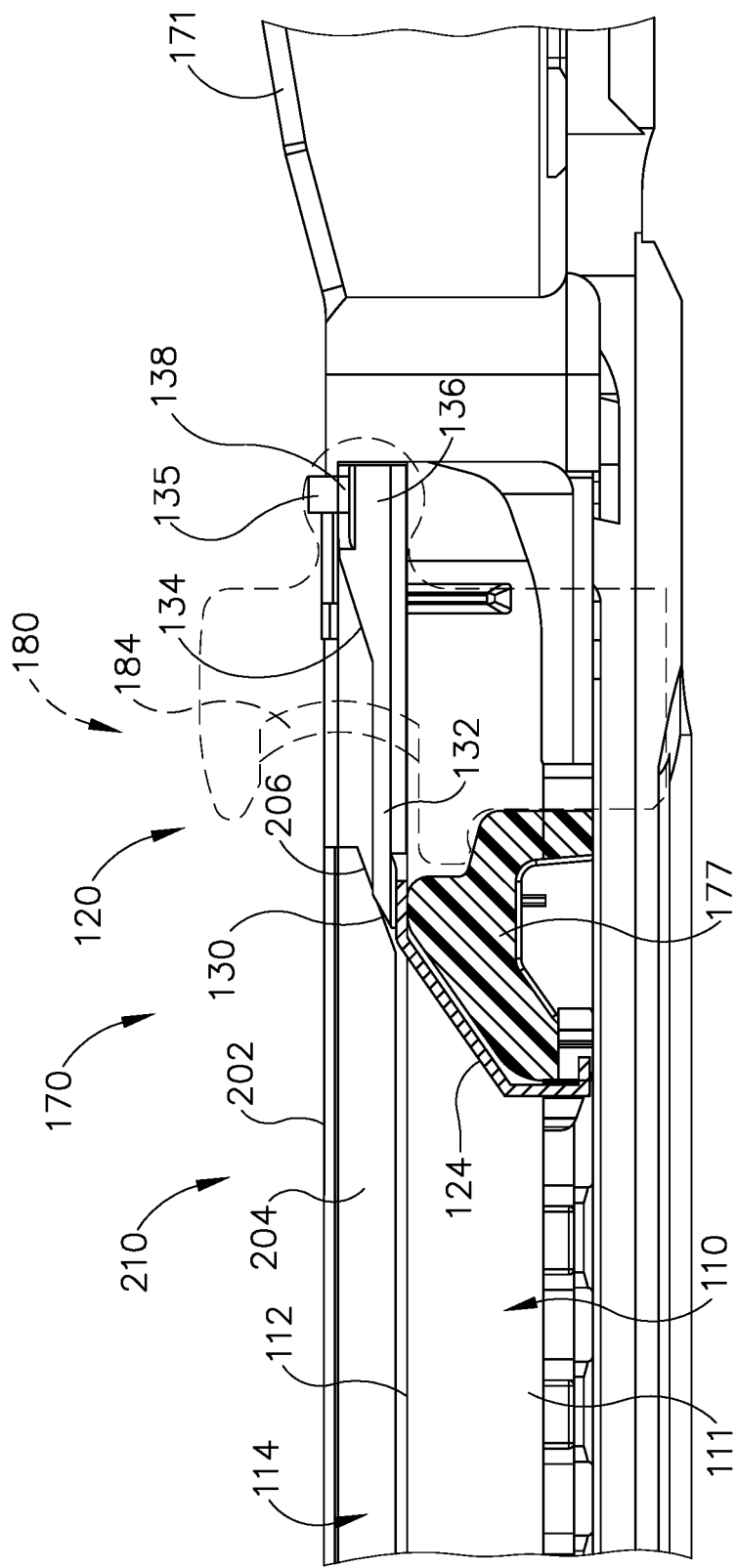
FIG. 16B depicts a cross-sectional side view of the end effector of FIG. 5, where the wedge sled of FIG. 14 is in a first actuated position in contact with the secondary folding sled of FIG. 9, where the secondary folding sled remains in the unactuated, proximal position.
Figure 16C:
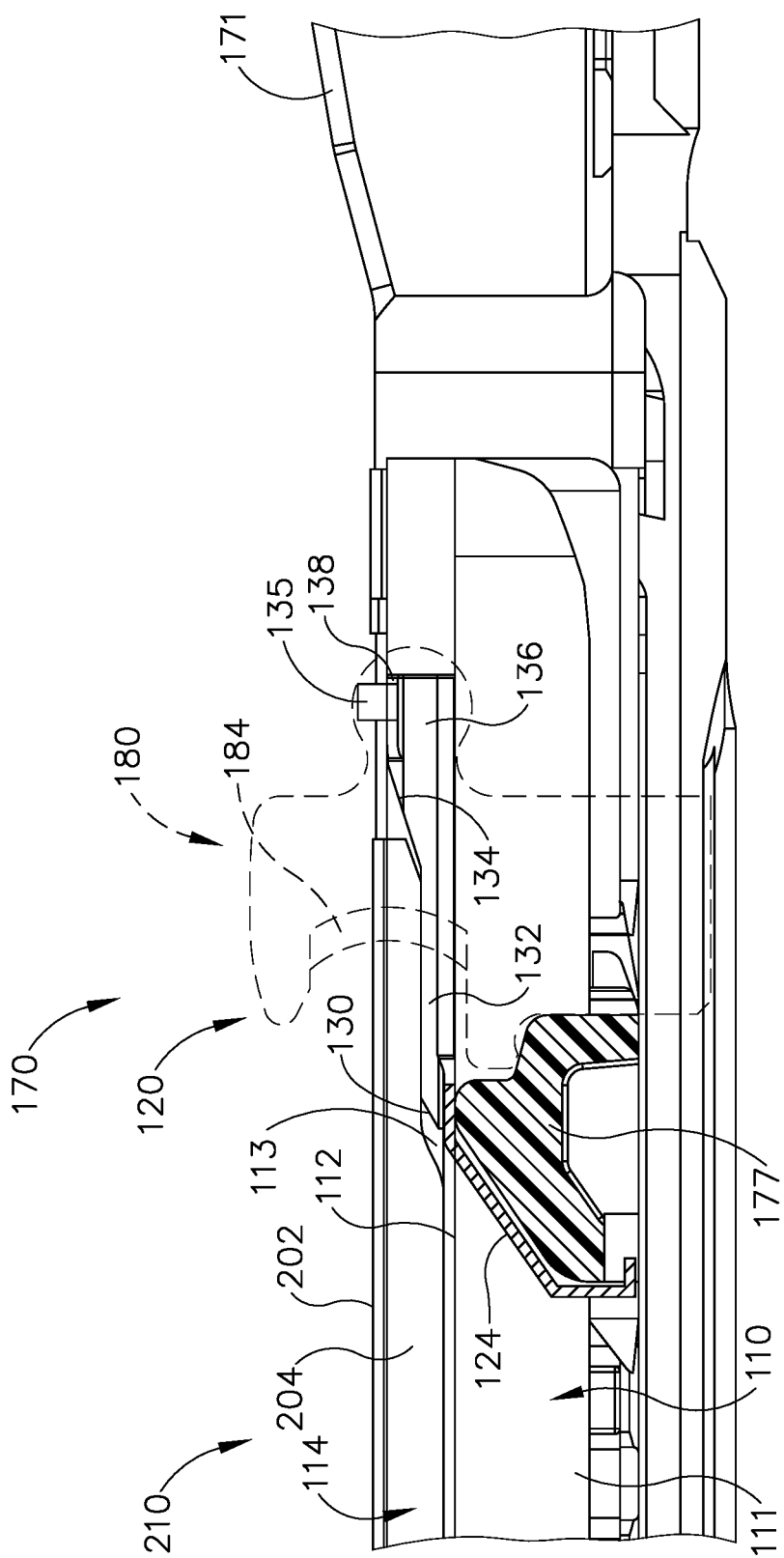
FIG. 16C depicts a cross-sectional side view of the end effector of FIG. 5, where the secondary folding sled of FIG. 9 and the wedge sled of FIG. 14 are in contact with each other, where the wedge sled is in a second actuated position, where the secondary folding sled is in a first actuated position.
Figure 17A:
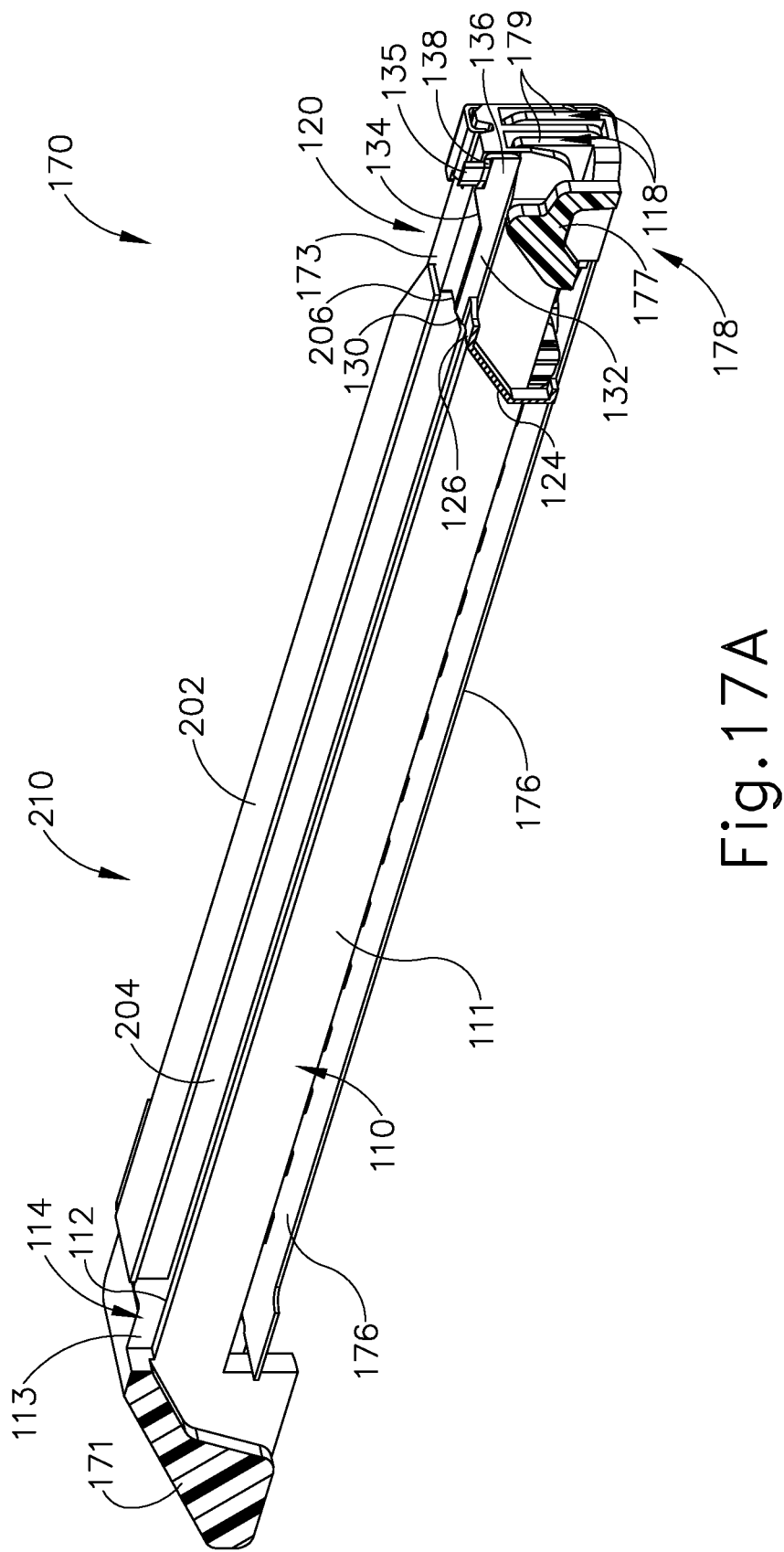
FIG. 17A depicts a cross-sectional perspective view of the end effector of FIG. 5, where the secondary folding sled of FIG. 9 and the wedge sled of FIG. 14 are each in the unactuated, proximal position.

FIGS. 16A and 17A show secondary sled driver (177) and folding sled (120) in an initial, unfired position. A user may then actuate knife member (180) in the distal direction within longitudinal channels (162, 172) in the distal direction. As mentioned above, wedge sled (178) is configured to actuate with knife member (180), such that secondary sled driver (177) also actuates in the distal direction within longitudinal channel (172). It should be understood that, as wedge sled (178) actuates from the position shown in FIGS. 16A and 17A to the position shown in FIGS. 16B and 17B, folding sled (120) remains stationary within longitudinal channel (172). Wedge sled (178) thus translates through a first range of motion without causing any corresponding movement of folding sled (120).

Figure 17B:
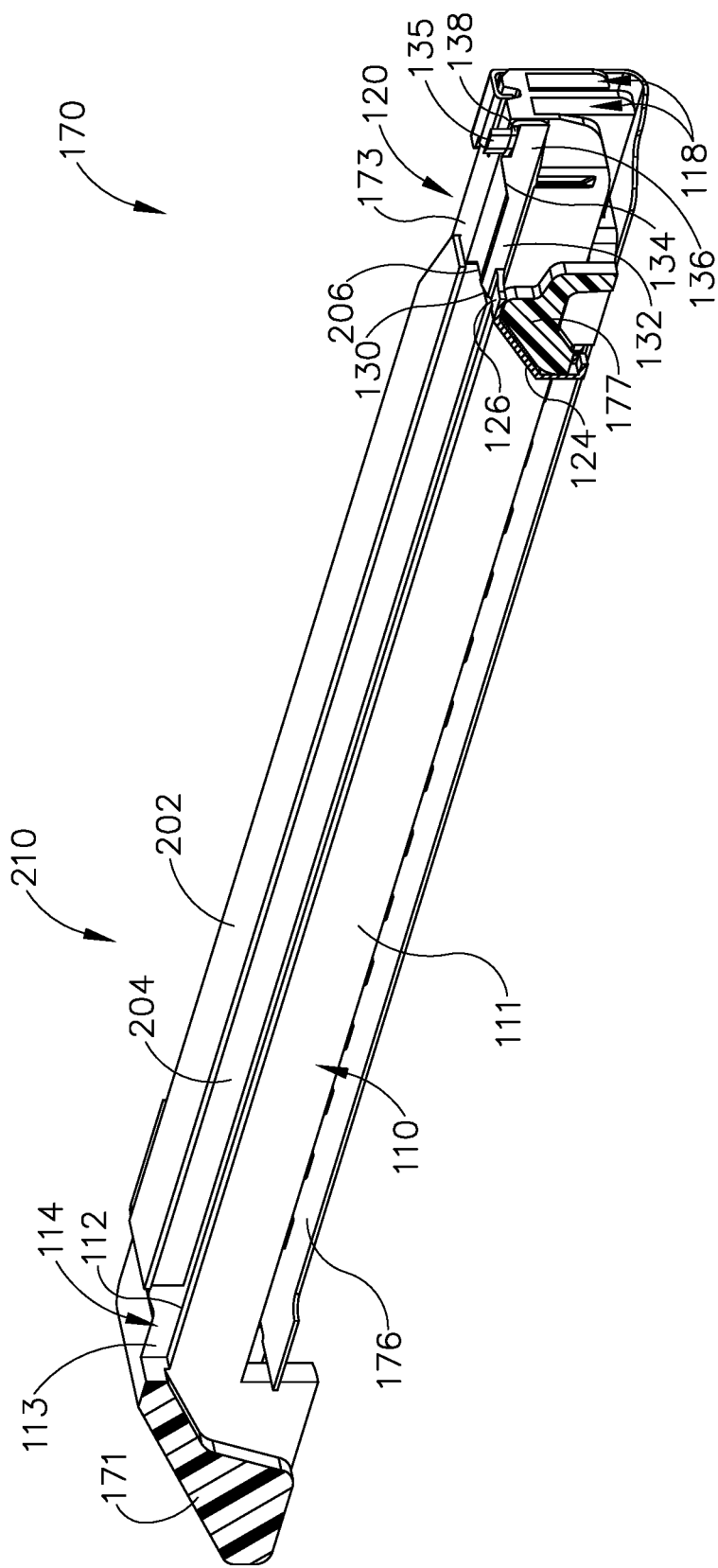
FIG. 17B depicts a cross-sectional perspective view of the end effector of FIG. 5, where the wedge sled of FIG. 14 is in the first actuated position in contact with the secondary folding sled of FIG. 9, where the secondary folding sled remains in the unactuated, proximal position.
Figure 17C:
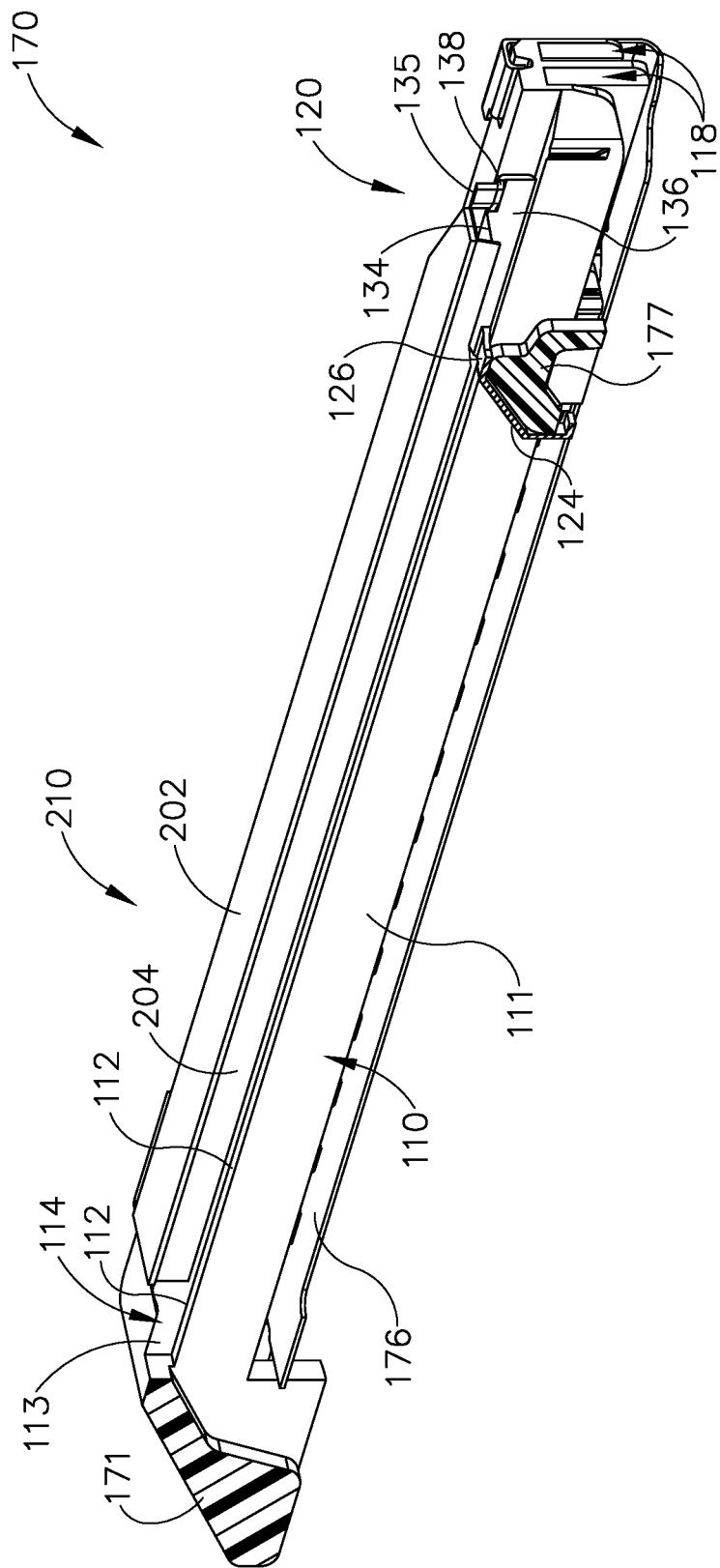
FIG. 17C depicts a cross-sectional perspective view of the end effector of FIG. 5, where the secondary folding sled of FIG.9 and the wedge sled of FIG. 14 are in contact with each other, where the wedge sled is in the second actuated position, where the secondary folding sled is in the first actuated position.

Once secondary sled driver (177) reaches the position shown in FIGS. 16B and 17B, secondary sled driver (177) is in contact with hooked projection (124) such that distal movement of sled driver (177) via actuation of knife member (180) causes corresponding distal movement of folding sled (120). In other words, wedge sled (170) and folding sled (120) now translate distally unitarily. It should be understood that distally presented cutting edge (184) of knife member (180) is located within slot (125) of folding sled (120) distally in relation to folding portion (136) of folding sled (120). Therefore, distally presented cutting edge (184) severs tissue ($T_1$, $T_2$) captured between anvil (160) and cartridge (170) before folding sled (120) folds an adjacent portion of bottom folding buttress (204) above deck (173). In other words, because distally presented cutting edge (184) is distal to folding portion (136), tissue ($T_1$, $T_2$) is first severed to create severed edges so that bottom folding buttress (204) may be folded against newly severed edges of tissue ($T_1$, $T_2$). It should also be understood that staples (190) are driven through tissue ($T_1$, $T_2$) before cutting edge (184) severs tissue ($T_1$, $T_2$). Thus, cutting edge (184) lags behind the driven staples (190) during actuation of end effector (140), while folding portion (136) lags behind cutting edge (184) during actuation of end effector (140).

As best seen in FIGS. 16A-16B and 17A-17B, the proximal end of bottom folding buttress (204) associated with wide vertical walls (113) has a proximal sloped portion (206). Distal sloped surface (130) of rail (132) may be dimensioned such that initial distal translation of folding sled (120) from the position shown in FIGS. 17A-17B causes distal sloped surface (130) of rail (132) to peel or fold proximal sloped portion (206) away from wide vertical walls (113). Alternatively, a portion of rail (132) may initially be located between proximal sloped portion (206) of bottom folding buttress (204) and wide vertical wall (113).

As best shown between FIGS. 16B-16C and 17B-17C, a user may further actuate knife member (180) in the distal direction, causing secondary sled driver (177) and folding sled (120) to unitarily translate. Specifically, translation of secondary sled driver (177) to the position shown in FIG. 16C and 17C causes rails (132) to further separate bottom folding buttress (204) from wide vertical wall (113).

It should be understood that during this translation, longitudinal translation of obliquely angled cam surface (179) is causing vertical translation of staple drivers (175), which drives staples (190) through buttress assembly (210) and ($T_1$, $T_2$), and against anvil (160) to deform legs of staple (190) back into tissue ($T_1$, $T_2$); additionally, distally presented cutting edge (184) is subsequently severing tissue captured between anvil (160) and cartridge (170).

Figure 16D:
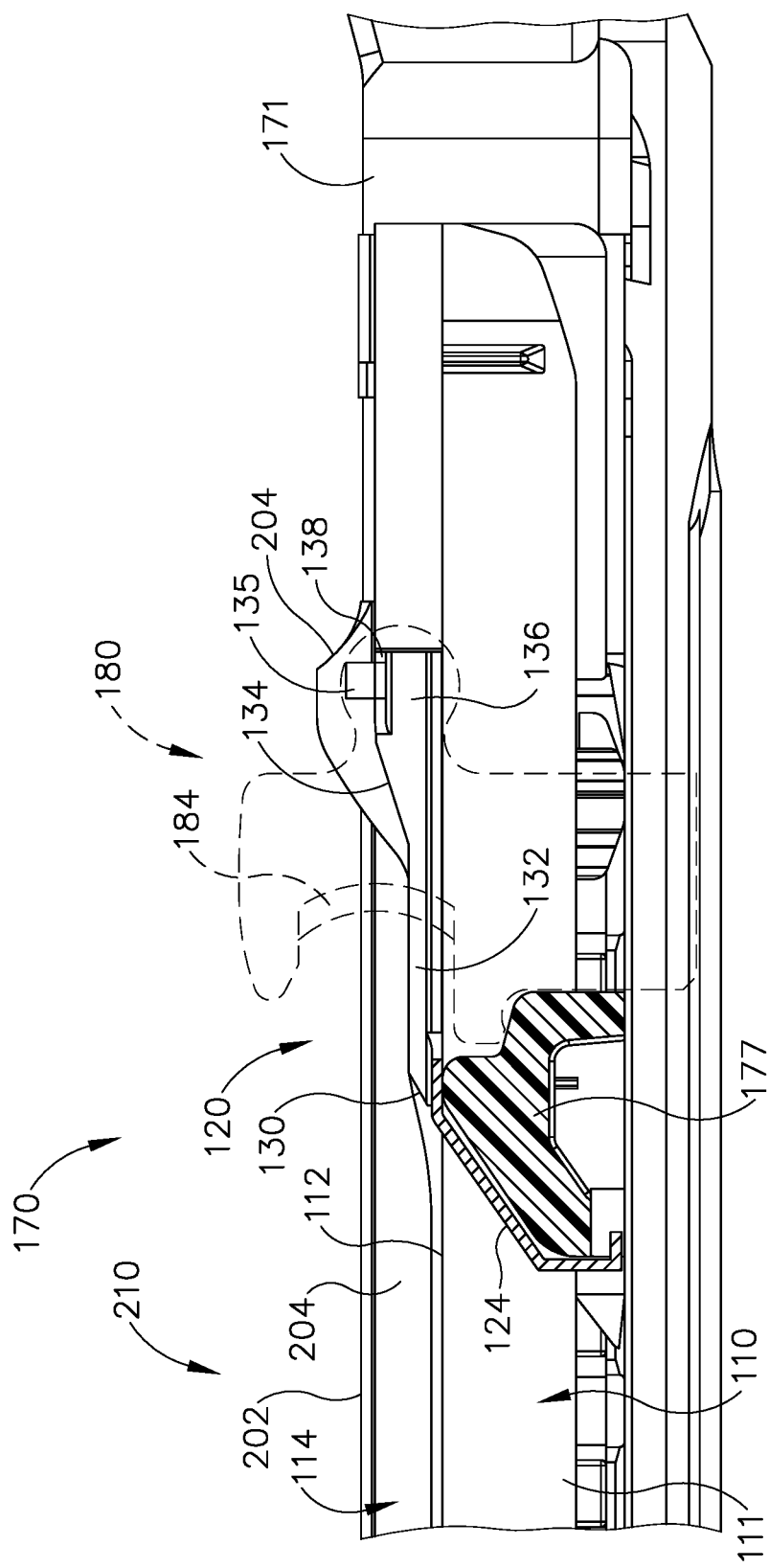
FIG. 16D depicts a cross-sectional side view of the end effector of FIG. 5, where the secondary folding sled of FIG. 9 and the wedge sled of FIG. 14 are in contact with each other, where the wedge sled is in a third actuated position, where the secondary folding sled is in a second actuated position.
Figure 17D:
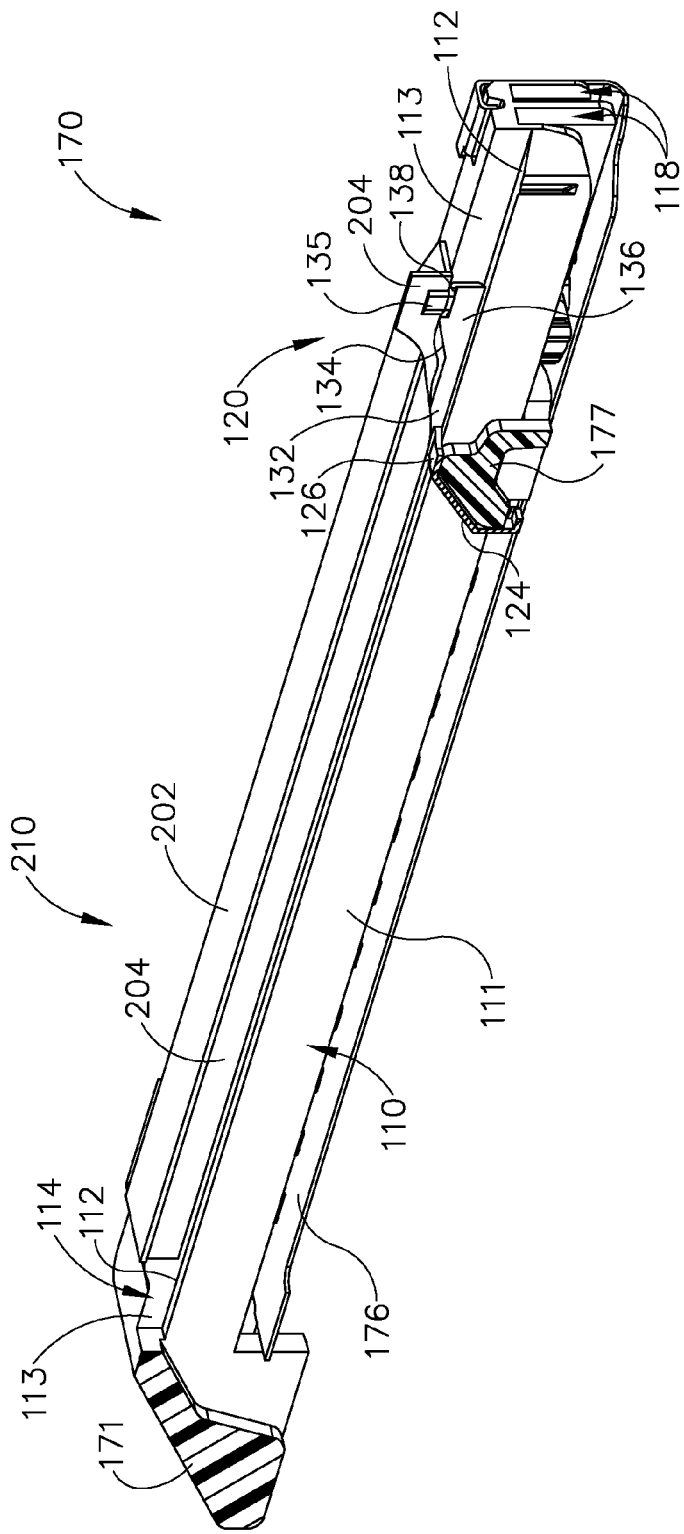
FIG. 17D depicts a cross-sectional perspective view of the end effector of FIG. 5, where the secondary folding sled of FIG. 9 and the wedge sled of FIG. 14 are in contact with each other, where the wedge sled is in the third actuated position, where the secondary folding sled is in the second actuated position.

A user may further actuate knife member (180) in the distal direction to the position shown in FIGS. 16D and 17D. At this point, a portion of bottom folding buttress (204) is located proximally relative to folding sled (120). As also seen in FIGS. 16D and 17D, the portion of bottom folding buttress (204) that is proximal to folding sled (120) has been folded to a position that is substantially perpendicular to deck (173).

Due to contact between sloped surface (134) of folding portion (136) and bottom folding buttress (204), bottom folding buttress (204) further separates and rotates away from vertical wall (113). Bottom folding buttress (204) subsequently further rotates to a position substantially parallel with deck (173) due to contact between bottom folding buttress (204) and inward projections (138). Then, bottom folding buttress (204) makes contact with fins (135), which props bottom folding buttress (204) above deck (173) such that bottom folding buttress (204) may make contact with newly severed edges of tissue ($T_1$, $T_2$).

It should be understood that during this translation, longitudinal translation of obliquely angled cam surface (179) is causing vertical translation of staple drivers (175), which drives staples (190) through buttress assembly (210) and ($T_1$, $T_2$), and against anvil (160) to deform legs of staple (190) back into tissue ($T_1$, $T_2$); additionally, distally presented cutting edge (184) is subsequently severing tissue ($T_1$, $T_2$) captured between anvil (160) and cartridge (170); then folding sled (120) is subsequently rotating bottom folding buttress (204) away from vertical wide walls (113), above deck (173), and against the edges of severed tissue ($T_1$, $T_2$). The portion of folding buttress (204) adjacent to deck (173) has already been stapled to tissue ($T_1$, $T_2$) while folding sled (120) is rotating the portion of folding buttress (204) associated with wide vertical wall (113).

It should be understood that the portion of bottom folding buttress (204) making contact with edges of severed tissue ($T_1$, $T_2$) may be coated with an adhesive to further promote bottom folding buttress (204) to secure against edges of severed tissue ($T_1$, $T_2$). Of course, any other suitable manner of securing bottom folding buttress (204) to edges of severed tissue ($T_1$, $T_2$) may be used as would be apparent to one having ordinary skill in the art. Additionally, the portion of bottom folding buttress (204) making contact with edges of severed tissue ($T_1$, $T_2$) may be coated with a substance that is configured to promote hemostasis and any other suitable therapeutic agent known to a person having ordinary skill in the art in view of the teachings herein.

Figure 16E:
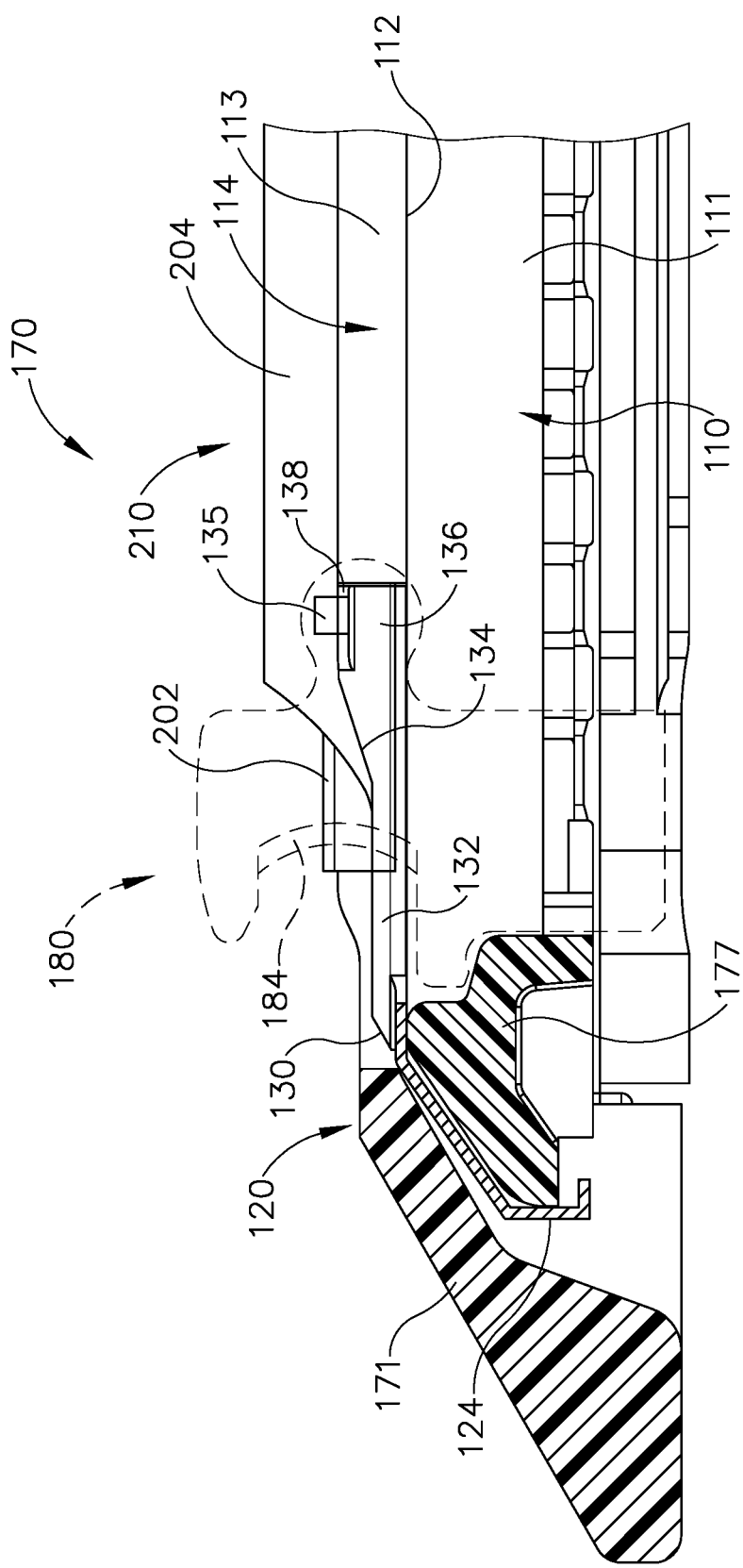
FIG. 16E depicts a cross-sectional side perspective view of the end effector of FIG. 5, where the secondary folding sled of FIG. 9 and the wedge sled of FIG. 14 are in contact with each other, where the wedge sled and the secondary folding sled are each in a distal-most position.
Figure 17E:
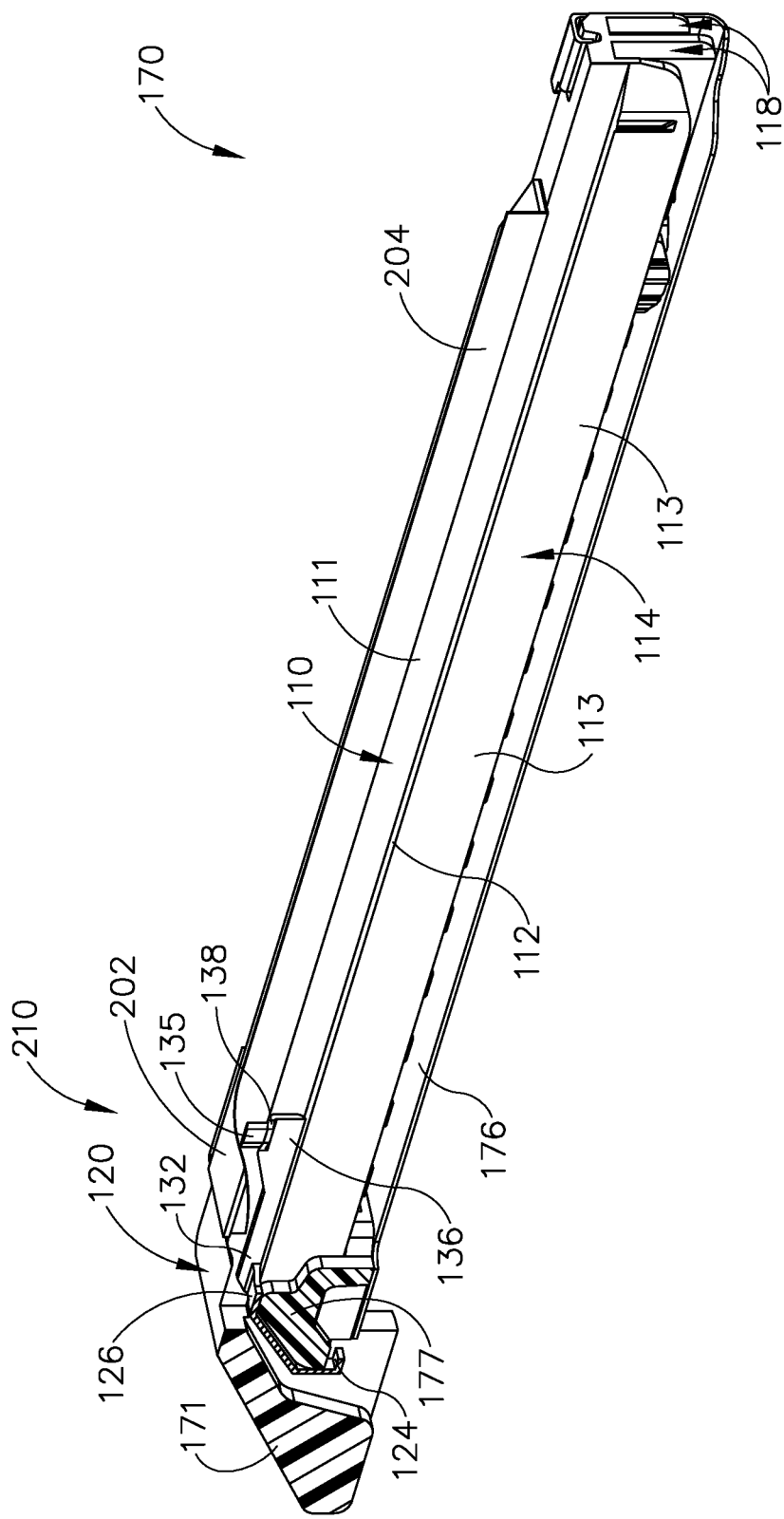
FIG. 17E depicts a cross-sectional perspective view of the end effector of FIG. 5, where the secondary folding sled of FIG. 9 and the wedge sled of FIG. 14 are in contact with each other, where the wedge sled and the secondary folding sled are each in the distal-most position.

As shown in FIGS. 16E and 17E, a user may further actuate knife member (180), secondary sled driver (177), and folding sled (120) to a distal position, thereby folding portions of bottom folding buttress (204) proximal to folding sled (120) against edges of severed tissue ($T_1$, $T_2$). It should be understood that while FIGS. 16E and 17E show portions of top buttress (202) still laying on top of deck (173), buttress assembly (210) would disengage end effector (140) similar to buttress assembly (110) described above in response to staples (190) forming to tissue ($T_1$, $T_2$).

FIGS. 18A-18E show a cross-sectional front view of a portion of cartridge body (171) as folding sled (120) longitudinally translates through that cross-sectional portion of cartridge body (171) to fold bottom folding buttress (204) against severed edges of tissue ($T_1$, $T_2$). As can be seen, anvil (160) also has a buttress assembly (200) located on underside (165). Layers of adjacent tissue ($T_1$, $T_2$) are located between buttress assemblies (200, 210).

Figure 18A:
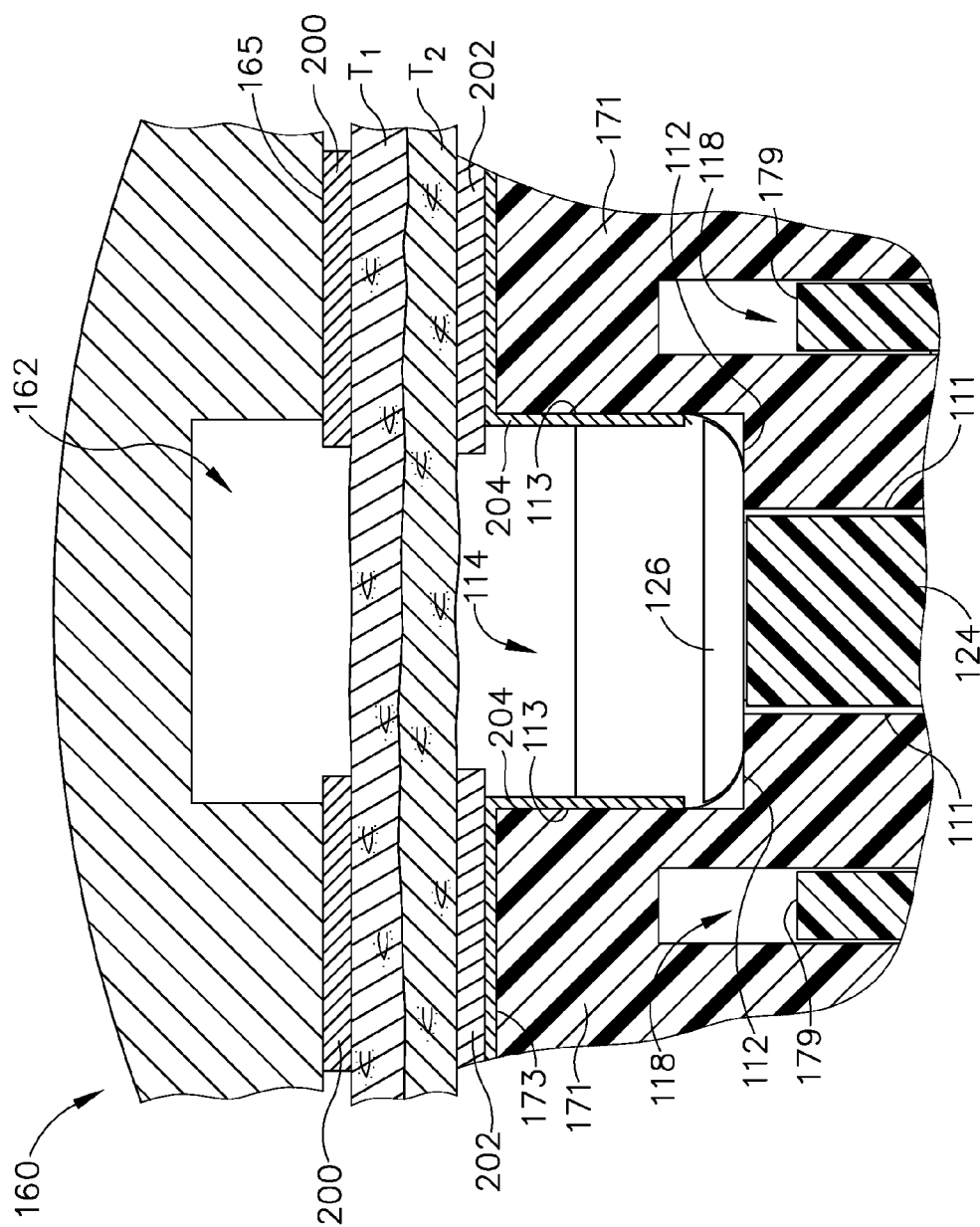
FIG. 18A depicts a cross-sectional front view of the end effector of FIG. 5, where the secondary folding sled of FIG. 9 is not in contact with the buttress of the end effector, where the knife member has not yet severed tissue.

In particular, FIG. 18A shows where only the portion of coupling member (126) distal to rails (132) is under bottom folding buttress (204). Therefore, coupling member (126) is not in contact with bottom folding buttress (204).

Figure 18B:
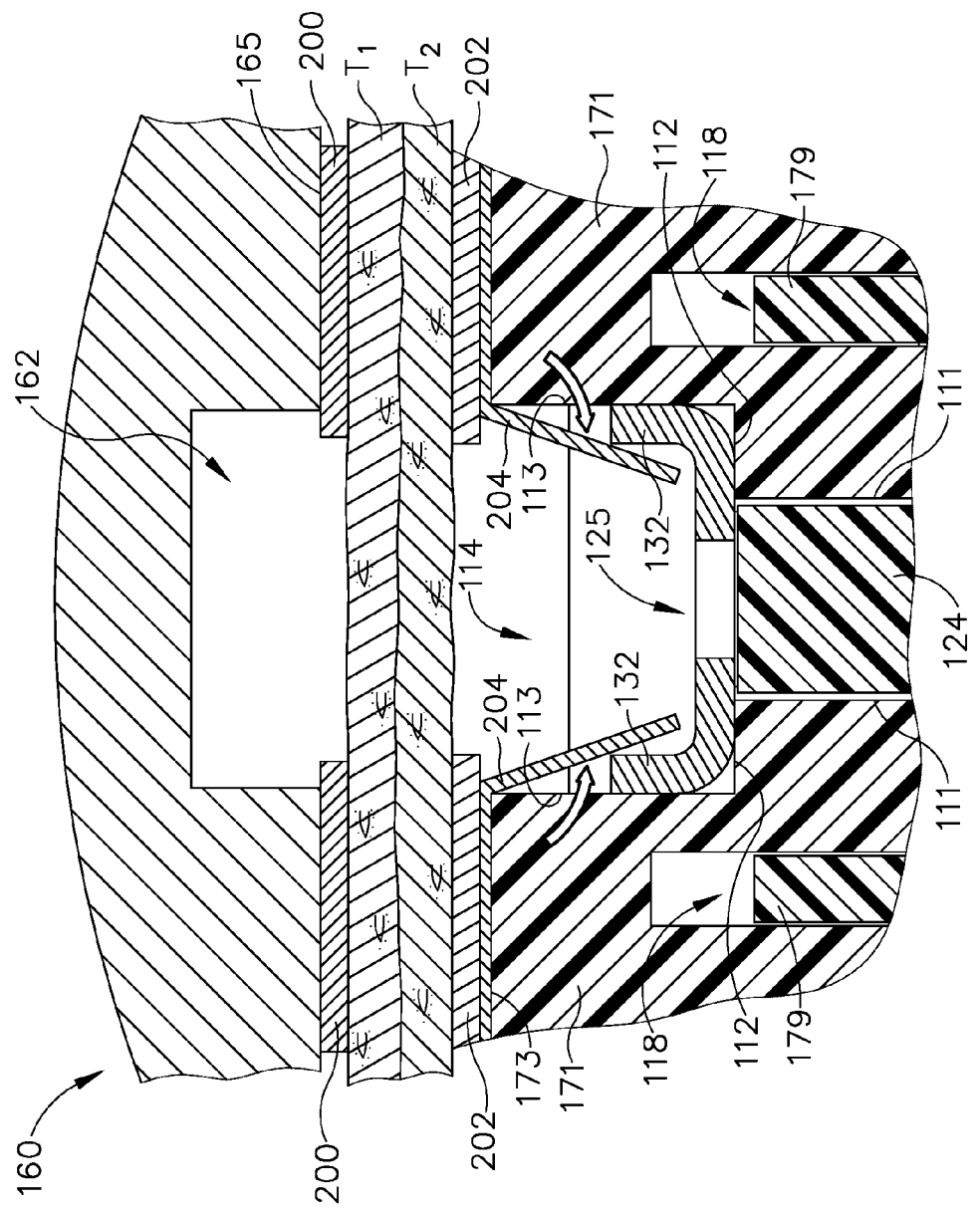
FIG. 18B depicts a cross-sectional front view of the end effector of FIG. 5, where the secondary folding sled of FIG. 9 has initially folded a portion of the buttress of the end effector, where the knife member has not yet severed tissue.

FIG. 18B shows folding sled (120) actuated to a position where rails (132) are in-between wide vertical walls (113) and bottom folding buttress (204). Therefore, the potion of bottom folding buttress (204) shown in FIG. 18B is rotated away from wide vertical walls (113), as previously described above. The portion of rails (132) shown in FIG. 18B is distal in relation to distally presented cutting edge (184), such that tissue ($T_1$, $T_2$) is yet to be severed.

FIG. 18C shows folding sled (120) actuated to a position where sloped surfaces (134) are in-between wide vertical walls (113) and bottom folding buttress (204). Therefore, the portion of bottom folding buttress (204) shown in FIG. 18C is rotated further away from wide vertical walls (113), as previously described above. The portion of sloped surface (134) is proximal in relation to distally presented cutting edge (184), such that tissue ($T_1$, $T_2$) has been severed and edges to which bottom folding buttress (204) will be folded against are formed.

Figure 18D:
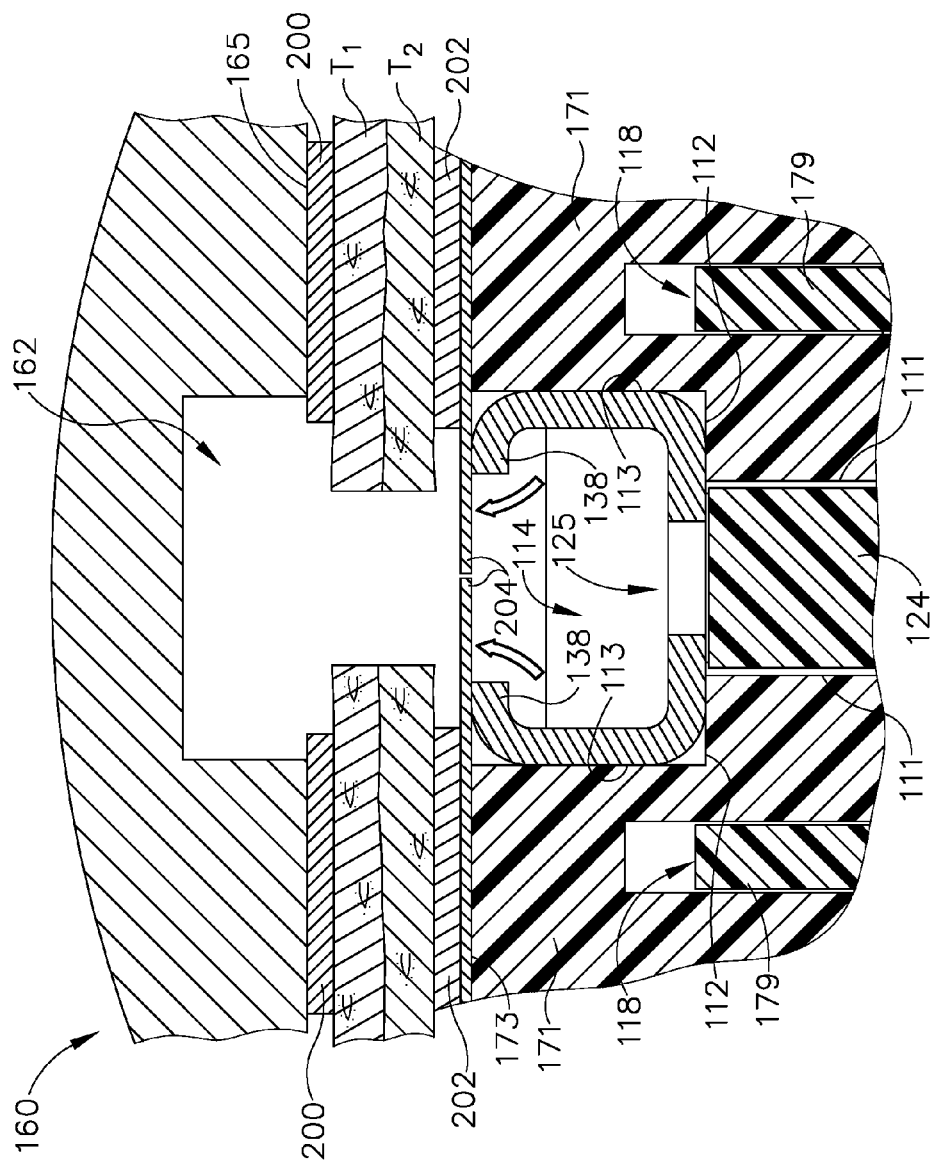
FIG. 18D depicts a cross-sectional front view of the end effector of FIG. 5, where the secondary folding sled of FIG. 9 has further folded a portion of the buttress of the end effector toward severed tissue.

FIG. 18D shows folding sled (120) actuated to a position where inward projections (138) are supporting bottom folding buttress (204) to a position substantially parallel with deck (173), as previously described above. It should be understood that severed edges of tissue ($T_1$, $T_2$) are still not yet in contact with bottom folding buttress (204)

Figure 18E:
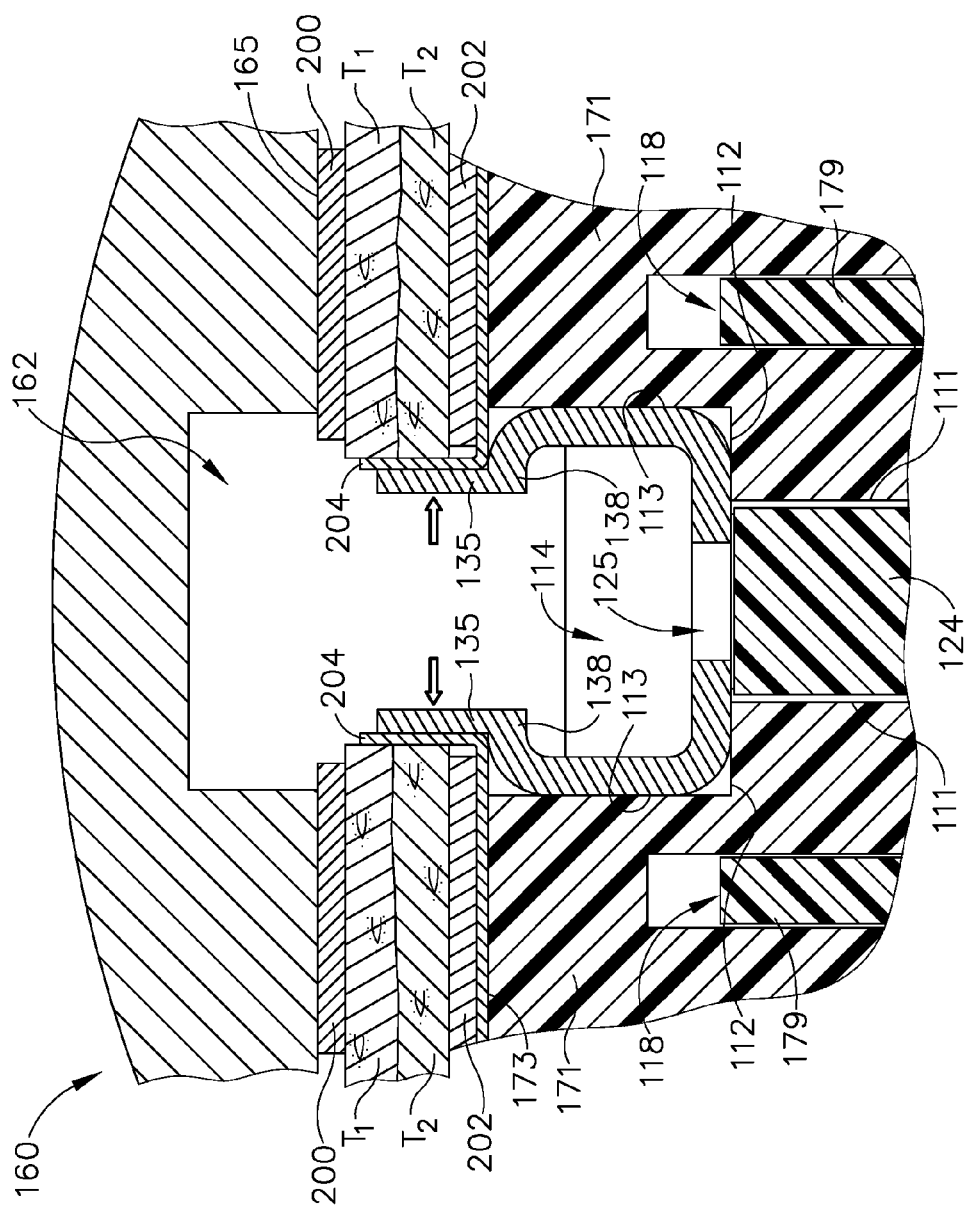
FIG. 18E depicts a cross-sectional front view of the end effector of FIG. 5, where the secondary folding sled of FIG. 9 has folded a portion of the buttress of the end effort against the edges of severed tissue.

FIG. 18E shows folding sled (120) actuated to a position where fins (135) have rotated bottom folding buttresses (204) to a position that is substantially perpendicular with and above deck (173). Additionally, fins (135) are positioned on top of inward projections (138) such that fins (135) push bottom folding buttress (204) against severed edges of tissue ($T_1$, $T_2$). Fins (135) also push both folding buttress (204) and severed edges of tissue ($T_1$, $T_2$) in the lateral direction away from longitudinal channel (172). Fins (135) may supply enough force against bottom folding buttress (204) and severed edges of tissue ($T_1$, $T_2$) such that folding buttress (204) is attached to severed edges. While fins (135) are shown as extending vertically upwardly in this example, some versions may provide fins (135) that extend obliquely outwardly, thereby enhancing the outward pressure applied by fins against folding buttress (204) to promote adhesion between folding buttress (204) and the severed edges of tissue ($T_1$, $T_2$). As yet another merely illustrative example, some versions of fins (135) may be curved outwardly or angled obliquely outwardly, such that distal portions of fins (135) apply less outward pressure than proximal portions of fins (135), and such that the outward pressure applied by fins (135) increases progressively as fins (135) travel along a given region of severed edges of tissue ($T_1$, $T_2$). Still other suitable configurations that may be provided for fins (135) will be apparent to those of ordinary skill in the art in view of the teachings herein.

Figure 19:
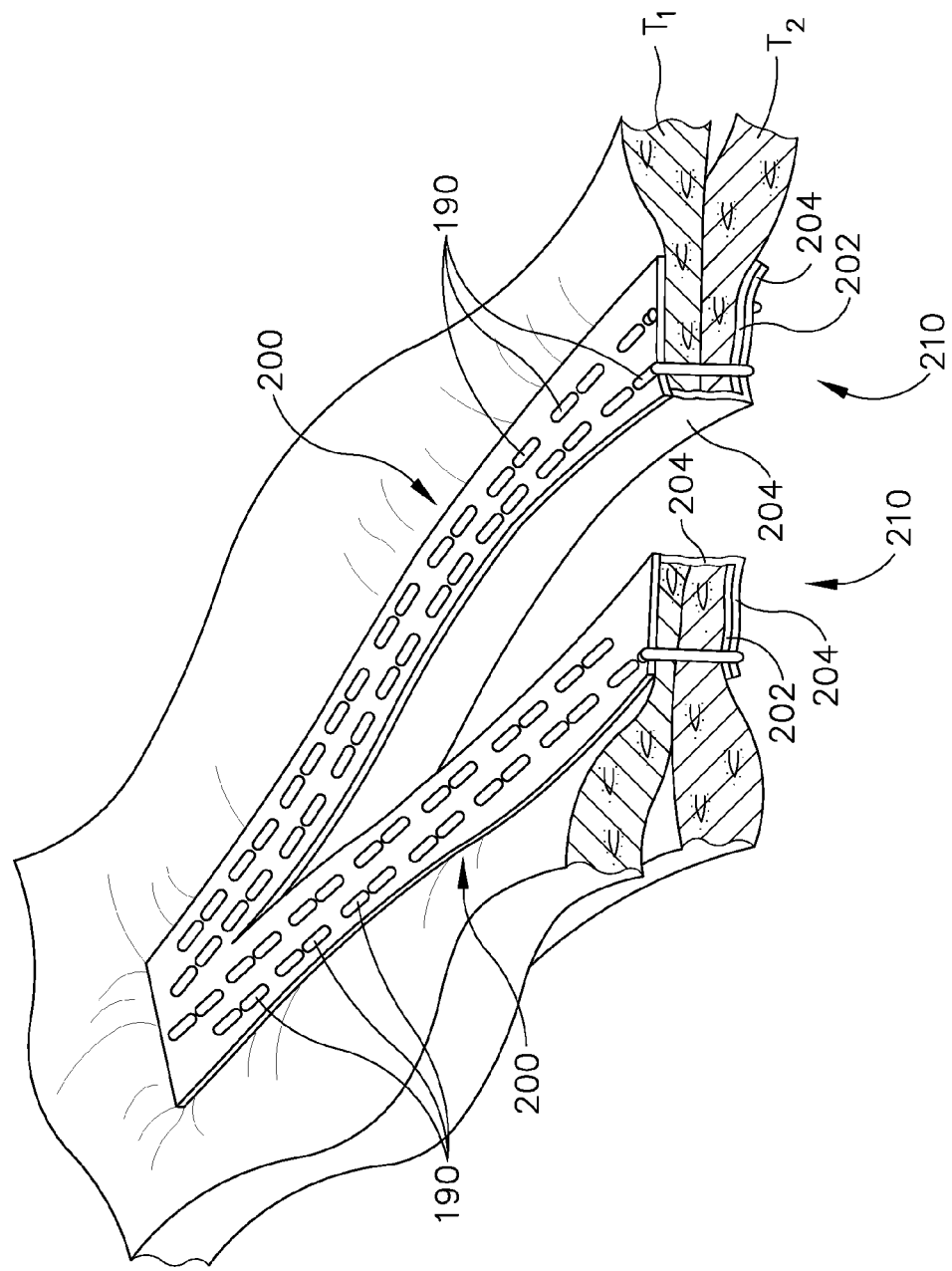
FIG. 19 depicts a perspective view of staples and the buttress assembly of the end effector of FIG. 5 having been secured to tissue by the end effector.

FIG. 19 shows the end result where buttress assembly (200, 210) are attached to tissue ($T_1$, $T_2$) and folding button buttress (204) is folded and attached to severed edges of tissue ($T_1$, $T_2$).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus, the apparatus comprising: (a) a body assembly; (b) a shaft extending distally from the body assembly; (c) an end effector attached to the shaft, wherein the end effector comprises: (i) a jaw, (ii) an anvil pivotable from an open position to a closed position relative to the jaw, and (iii) a knife member configured to translate relative to the anvil in order to sever tissue; and (d) a cartridge defining a longitudinal channel, wherein the knife member is configured to translate within the longitudinal channel, wherein the cartridge comprises: (i) a deck comprising an upper surface facing toward the anvil, (ii) a buttress assembly, wherein a first portion of the buttress assembly is positioned on top of the deck, wherein a second portion of the buttress assembly is positioned within the longitudinal channel, and (iii) a folding sled configured to translate within the longitudinal channel to move the second portion of the buttress assembly to a position that is above the deck in response to actuation of the knife member.

Example 2

The apparatus of Example 1, wherein the end effector further comprises a wedge sled configured to actuate with the knife member, wherein the cartridge further comprises a plurality of staple pockets and a plurality of staples located within the plurality of staple pockets, wherein the wedge sled is configured to drive the plurality of staples though the plurality of staple pockets.

Example 3

The apparatus of any one or more of Examples 1 through 2, wherein the folding sled comprises a projection, wherein the knife member is configured drive the folding sled via the projection.

Example 4

The apparatus of Example 3, wherein the knife member is configured to translate through a first range of motion and a second range of motion, wherein the folding sled is configured to remain stationary while the knife member translates through the first range of motion.

Example 5

The apparatus of Example 4, wherein the folding sled is configured to unitarily translate with knife member when knife member translates through the second range of motion.

Example 6

The apparatus of any one or more of Examples 3 through 5, wherein the folding sled further comprises a folding arm extending proximally relative to the projection.

Example 7

The apparatus of Example 6, wherein the longitudinal channel includes a step defining a narrow portion of the longitudinal channel and a wide portion of the longitudinal channel, wherein the projection is slidably housed within the narrow portion of the longitudinal channel.

Example 8

The apparatus of Example 7, wherein the folding arm rests on the step and within the wide portion of the longitudinal channel.

Example 9

The apparatus of any one or more of Examples 6 through 8, wherein the folding arm comprises a proximal end, wherein the knife member is configured to sever tissue distal to the proximal end of the folding arm.

Example 10

The apparatus of any one or more of Examples 6 through 9, wherein the folding arm further comprises a sloped surface configured to rotate the second portion of the buttress assembly relative to the deck.

Example 11

The apparatus of Example 10, wherein the folding arm further comprises an inward projection, wherein the inward projection is configured to move the second portion of the buttress assembly to a position that is substantially parallel with the deck.

Example 12

The apparatus of Example 11, wherein the folding arm further comprises a fin extending above the inward projection, wherein the fin is configured to move the second portion of the buttress assembly to a position that is above the deck and substantially perpendicular to the deck.

Example 13

The apparatus of Example 12, wherein the second portion of the buttress comprises an adhesive configured to attach the second portion of severed tissue.

Example 14

The apparatus of any one or more of Examples 1 through 13, wherein the anvil comprises an underside configured to face the deck when the anvil is in the closed position, wherein the anvil include a buttress assembly attached to the underside.

Example 15

The apparatus of any one or more of Examples 1 through 14, wherein the first portion is unitarily connected to the second portion.

Example 16

The apparatus of any one or more of Examples 1 through 15, wherein the knife member comprises a distally presented cutting edge, wherein a first portion of the folding sled is proximal to the distally presented cutting edge, wherein a second portion of the folding sled is distal to the distally presented cutting edge.

Example 17

An apparatus, the apparatus comprising: (a) a body assembly; (b) a shaft extending distally from the body assembly; (c) an end effector attached to the shaft, wherein the end effector comprises: (i) a jaw, (ii) an anvil pivotable from an open position to a closed position relative to the jaw, (iii) a knife member configured to translate relative to the anvil in order to sever tissue, and (iv) a wedge sled configured to translate with the knife member; and (d) a cartridge defining a longitudinal channel, wherein the knife member is configured to translate within the longitudinal channel, wherein the cartridge comprises: (i) a deck comprising an upper surface facing toward the anvil in the closed position, (ii) a plurality of staple pockets, (iii) a plurality of staples located within the plurality of staple pockets, the wedge sled is operable to drive the plurality of staples out of the plurality of staple pockets, (iv) a buttress assembly, wherein a first portion of the buttress assembly is positioned on top of the deck, wherein a second portion of the buttress assembly is positioned within the longitudinal channel, and (v) a folding sled configured to translate within the longitudinal channel to move the second portion of the buttress assembly to a position that is above the deck.

Example 18

The apparatus of Example 17, wherein the folding sled comprises a folding arm and a projection, wherein the projection is configured to receive a portion of the wedge sled, wherein the folding arm is configured to be proximal in relation to a distal end of knife member when the projection receives the wedge sled.

Example 19

The apparatus of any one or more of Examples 17 through 18, wherein the wedge sled is configured to drive the folding sled.

Example 20

An apparatus, the apparatus comprising: (a) a body assembly; (b) a shaft extending distally from the body assembly; (c) an end effector attached to the shaft, wherein the end effector comprises: (i) a jaw, (ii) an anvil pivotable from an open position to a closed position relative to the jaw, and (iii) a knife member configured to translate relative to the anvil in order to sever tissue; and (d) a cartridge releasably engaged with the jaw, wherein the cartridge defines a longitudinal channel, wherein the knife member is configured to translate within the longitudinal channel, wherein the cartridge comprises: (i) a deck comprising an upper surface facing toward the anvil, (ii) a buttress assembly, wherein a first portion of the buttress assembly is positioned on top of the deck, wherein a second portion of the buttress assembly is positioned within the longitudinal channel, wherein the first portion and the second portion are connected to each other, and (iii) a folding sled comprising a folding member, wherein the folding member is configured to translate within the longitudinal channel proximally in relation to the a distal end of the knife member in order to move the second portion of the buttress assembly to a position that is above the deck.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, the apparatus comprising:
   (a) a body assembly;
   (b) a shaft extending distally from the body assembly;
   (c) an end effector attached to the shaft, wherein the end effector comprises:
      (i) a jaw,
      (ii) an anvil pivotable from an open position to a closed position relative to the jaw, and
      (iii) a knife member configured to translate relative to the anvil in order to sever tissue; and
   (d) a cartridge defining a longitudinal channel, wherein the knife member is configured to translate within the longitudinal channel, wherein the cartridge comprises:
      (i) a deck comprising an upper surface facing toward the anvil,
      (ii) a buttress assembly, wherein a first portion of the buttress assembly is positioned on top of the deck, wherein a second portion of the buttress assembly is positioned within the longitudinal channel, and
      (iii) a folding sled configured to translate within the longitudinal channel to move the second portion of the buttress assembly to a position that is above the deck in response to actuation of the knife member.

2. The apparatus of claim 1, wherein the end effector further comprises a wedge sled configured to actuate with the knife member, wherein the cartridge further comprises a plurality of staple pockets and a plurality of staples located within the plurality of staple pockets, wherein the wedge sled is configured to drive the plurality of staples though the plurality of staple pockets.

3. The apparatus of claim 1, wherein the folding sled comprises a projection, wherein the knife member is configured to drive the folding sled via the projection.

4. The apparatus of claim 3, wherein the knife member is configured to translate through a first range of motion and a second range of motion, wherein the folding sled is configured to remain stationary while the knife member translates through the first range of motion.

5. The apparatus of claim 4, wherein the folding sled is configured to unitarily translate with knife member when knife member translates through the second range of motion.

6. The apparatus of claim 3, wherein the folding sled further comprises a folding arm extending proximally relative to the projection.

7. The apparatus of claim 6, wherein the longitudinal channel includes a step defining a narrow portion of the longitudinal channel and a wide portion of the longitudinal channel, wherein the projection is slidably housed within the narrow portion of the longitudinal channel.

8. The apparatus of claim 7, wherein the folding arm rests on the step and within the wide portion of the longitudinal channel.

9. The apparatus of claim 6, wherein the folding arm comprises a proximal end, wherein the knife member is configured to sever tissue distal to the proximal end of the folding arm.

10. The apparatus of claim 6, wherein the folding arm further comprises a sloped surface configured to rotate the second portion of the buttress assembly relative to the deck.

11. The apparatus of claim 10, wherein the folding arm further comprises an inward projection, wherein the inward projection is configured to move the second portion of the buttress assembly to a position that is substantially parallel with the deck.

12. The apparatus of claim 11, wherein the folding arm further comprises a fin extending above the inward projection, wherein the fin is configured to move the second portion of the buttress assembly to a position that is above the deck and substantially perpendicular to the deck.

13. The apparatus of claim 12, wherein the second portion of the buttress comprises an adhesive configured to attach the second portion of severed tissue.

14. The apparatus of claim 1, wherein the anvil comprises an underside configured to face the deck when the anvil is in the closed position, wherein the anvil include a buttress assembly attached to the underside.

15. The apparatus of claim 1, wherein the first portion is unitarily connected to the second portion.

16. The apparatus of claim 1, wherein the knife member comprises a distally presented cutting edge, wherein a first portion of the folding sled is proximal to the distally presented cutting edge, wherein a second portion of the folding sled is distal to the distally presented cutting edge.

17. An apparatus, the apparatus comprising:
(a) a body assembly;
(b) a shaft extending distally from the body assembly;
(c) an end effector attached to the shaft, wherein the end effector comprises:
 (i) a jaw,
 (ii) an anvil pivotable from an open position to a closed position relative to the jaw,
 (iii) a knife member configured to translate relative to the anvil in order to sever tissue, and
 (iv) a wedge sled configured to translate with the knife member; and
(d) a cartridge defining a longitudinal channel, wherein the knife member is configured to translate within the longitudinal channel, wherein the cartridge comprises:
 (i) a deck comprising an upper surface facing toward the anvil in the closed position,
 (ii) a plurality of staple pockets,
 (iii) a plurality of staples located within the plurality of staple pockets, the wedge sled is operable to drive the plurality of staples out of the plurality of staple pockets,
 (iv) a buttress assembly, wherein a first portion of the buttress assembly is positioned on top of the deck, wherein a second portion of the buttress assembly is positioned within the longitudinal channel, and
 (v) a folding sled configured to translate within the longitudinal channel to move the second portion of the buttress assembly to a position that is above the deck.

18. The apparatus of claim 17, wherein the folding sled comprises a folding arm and a projection, wherein the projection is configured to receive a portion of the wedge sled, wherein the folding arm is configured to be proximal in relation to a distal end of knife member when the projection receives the wedge sled.

19. The apparatus of claim 17, wherein the wedge sled is configured to drive the folding sled.

20. An apparatus, the apparatus comprising:
(a) a body assembly;
(b) a shaft extending distally from the body assembly;
(c) an end effector attached to the shaft, wherein the end effector comprises:
 (i) a jaw,
 (ii) an anvil pivotable from an open position to a closed position relative to the jaw, and
 (iii) a knife member configured to translate relative to the anvil in order to sever tissue; and
(d) a cartridge releasably engaged with the jaw, wherein the cartridge defines a longitudinal channel, wherein the knife member is configured to translate within the longitudinal channel, wherein the cartridge comprises:
 (i) a deck comprising an upper surface facing toward the anvil,
 (ii) a buttress assembly, wherein a first portion of the buttress assembly is positioned on top of the deck, wherein a second portion of the buttress assembly is positioned within the longitudinal channel, wherein the first portion and the second portion are connected to each other, and
 (iii) a folding sled comprising a folding member, wherein the folding member is configured to translate within the longitudinal channel proximally in relation to the a distal end of the knife member in order to move the second portion of the buttress assembly to a position that is above the deck.

\* \* \* \* \*